(12) United States Patent
Horikiri et al.

(10) Patent No.: US 9,099,656 B2
(45) Date of Patent: Aug. 4, 2015

(54) ORGANIC COMPOUND AND ORGANIC LIGHT-EMITTING DEVICE INCLUDING SAME

(75) Inventors: Tomonari Horikiri, Chiba (JP); Jun Kamatani, Tokyo (JP); Masanori Muratsubaki, Hachioji (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 367 days.

(21) Appl. No.: 13/813,621

(22) PCT Filed: Jul. 26, 2011

(86) PCT No.: PCT/JP2011/067578
§ 371 (c)(1),
(2), (4) Date: Jan. 31, 2013

(87) PCT Pub. No.: WO2012/017977
PCT Pub. Date: Feb. 9, 2012

(65) Prior Publication Data
US 2013/0126857 A1 May 23, 2013

(30) Foreign Application Priority Data
Aug. 3, 2010 (JP) .................................. 2010-174838

(51) Int. Cl.
H01L 51/50 (2006.01)
C07C 13/62 (2006.01)
C09K 11/06 (2006.01)
H01L 51/00 (2006.01)
H05B 33/14 (2006.01)

(52) U.S. Cl.
CPC ............ H01L 51/0056 (2013.01); C07C 13/62 (2013.01); C09K 11/06 (2013.01);
(Continued)

(58) Field of Classification Search
CPC .... C07C 13/62; C07C 2103/54; C09K 11/06; C09K 2211/1011; C09K 2211/1014; C09K 2211/1029; H01L 51/0056; H01L 51/0067; H01L 51/0068; H01L 51/0072; H05B 33/14
See application file for complete search history.

(56) References Cited
U.S. PATENT DOCUMENTS
8,628,863 B2 * 1/2014 Sekiguchi et al. ............ 428/690
(Continued)

FOREIGN PATENT DOCUMENTS
JP 10-189247 A 7/1998
(Continued)

OTHER PUBLICATIONS
Chang et al., "An Important Key to Design Molecules with Small Internal Reorganization Energy: Strong Nonbonding Character in Frontier Orbitals," Journal of Physical Chemistry Letters, Jan. 7, 2010, pp. 116-121.

*Primary Examiner* — Dawn L. Garrett
(74) *Attorney, Agent, or Firm* — Canon USA, Inc. IP Division

(57) ABSTRACT

A novel organic compound suitably used for a green-light-emitting device and an organic light-emitting device are provided.
An organic light-emitting device and an image display apparatus containing a naphtho[2',3':5,6]indeno[1,2,3-cd]pyrene derivative represented by general formula (1) as a dopant:

[Chem. 1]

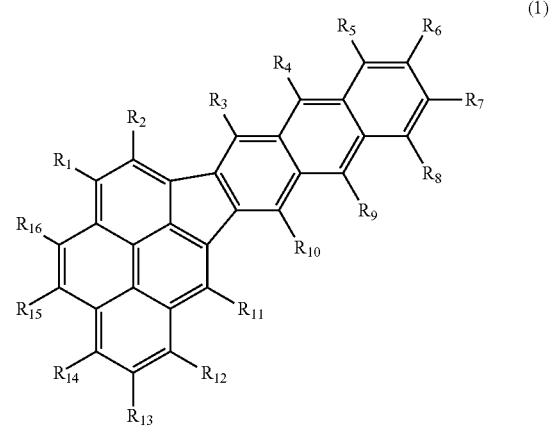

(1)

wherein in general formula (1), $R_1$ to $R_{16}$ are each independently selected from a hydrogen atom, a halogen atom, substituted or unsubstituted alkyl groups, substituted or unsubstituted alkoxy groups, substituted or unsubstituted amino groups, substituted or unsubstituted aryl groups, and substituted or unsubstituted heterocyclic groups, and at least one of $R_3$, $R_4$, $R_9$, and $R_{10}$ is selected from substituted or unsubstituted aryl groups and substituted or unsubstituted heterocyclic groups.

10 Claims, 1 Drawing Sheet

(52) U.S. Cl.
CPC ........ *H01L51/0067* (2013.01); *H01L 51/0068* (2013.01); *H01L 51/0072* (2013.01); *H05B 33/14* (2013.01); *C07C 2103/54* (2013.01); *C09K 2211/1011* (2013.01); *C09K 2211/1014* (2013.01); *C09K 2211/1029* (2013.01)

(56) References Cited

U.S. PATENT DOCUMENTS 8,759,590 B2 * 6/2014 Ikeda et al. .................. 564/426
2002/0168549 A1 * 11/2002 Iwata et al. ............ 428/694 ML
2004/0076853 A1 * 4/2004 Jarikov ........................ 428/690

FOREIGN PATENT DOCUMENTS

| JP | 2008-305935 A | 12/2008 |
| JP | 2009-009966 A | 1/2009 |
| WO | 2010/061952 A1 | 6/2010 |
| WO | 2011/036868 A1 | 3/2011 |

* cited by examiner

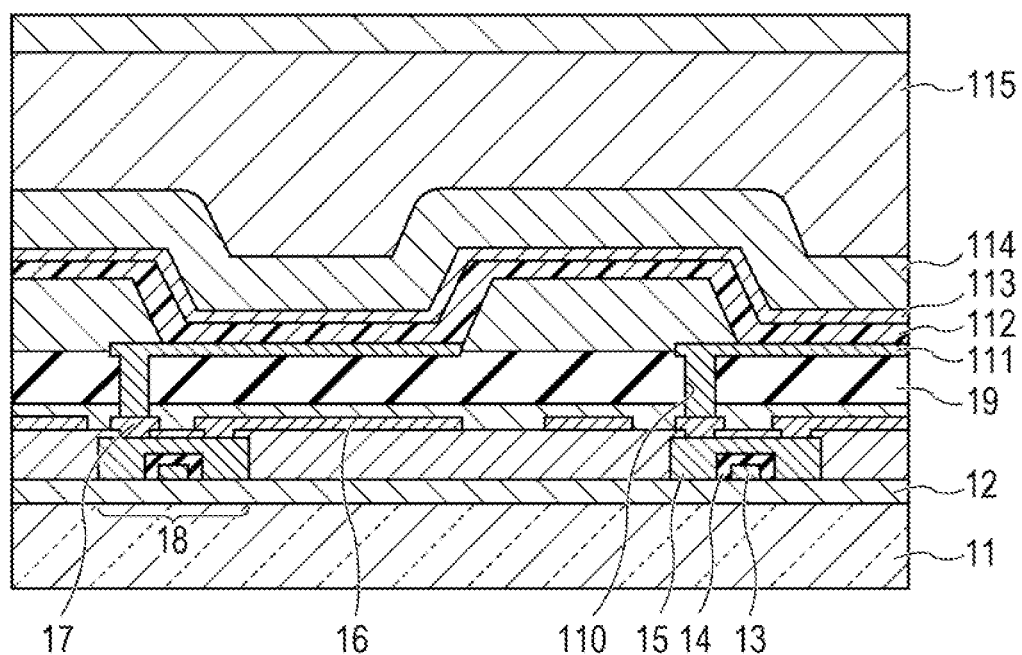

ORGANIC COMPOUND AND ORGANIC LIGHT-EMITTING DEVICE INCLUDING SAME

TECHNICAL FIELD

The present invention relates to a novel compound, a naphtho[2',3':5,6]indeno[1,2,3-cd]pyrene derivative, and to an organic light-emitting device including the novel compound.

BACKGROUND ART

An organic light-emitting device includes a thin film which contains a fluorescent organic compound and which is arranged between an anode and a cathode. The injection of electrons and holes from the respective electrodes produces excitons of the fluorescent organic compound. Light emitted when the excitons return to the ground state is used.

Among organic light-emitting devices, in particular, organic light-emitting devices using electroluminescence are sometimes referred to as organic electroluminescent devices or organic EL devices.

The characteristic features of organic light-emitting devices include high luminance at a low applied voltage. Furthermore, the use of organic light-emitting devices enables us to produce rapid-response, thin, lightweight light-emitting apparatuses that emit light beams with a variety of emission wavelengths. So, organic light-emitting devices will be used for a wide variety of applications.

For the reasons, novel compounds, which are important in the production of high-performance organic light-emitting devices, have been intensively developed.

For example, PTL 1 describes a benzo[k]fluoranthene derivative serving as a compound used in a light-emitting layer.

There is still room for improvement in the organic compound described in PTL 1 and organic light-emitting devices including the compound from the viewpoint of achieving practical use. Specifically, organic light-emitting devices are required to have a higher-intensity optical output or higher photoconversion efficiency. Furthermore, it is necessary to minimize the variation with time by prolonged use and to improve durability, for example, the resistance to degradation due to oxygen, humidity, and so forth.

When application of organic light-emitting devices to image display apparatuses, such as full-color displays, is contemplated, it is necessary for organic light-emitting devices to have satisfactory color purity and emit blue light with high efficiency. However, these problems are not fully solved.

Accordingly, an organic light-emitting device having high color purity, luminous efficiency, and durability and a novel compound used to produce the device have been demanded.

CITATION LIST

Patent Literature

PTL 1 Japanese Patent Laid-Open No. 10-189247

SUMMARY OF INVENTION

Technical Problem

Aspects of the present invention provide a novel organic compound and a device having high luminous efficiency and a low driving voltage, i.e., a device having high luminous efficiency and emitting light in a light amount required even if the device is driven at a low voltage.

Solution to Problem

A naphtho[2',3':5,6]indeno[1,2,3-cd]pyrene derivative according to aspects of the present invention is represented by general formula (1):

[Chem. 1]

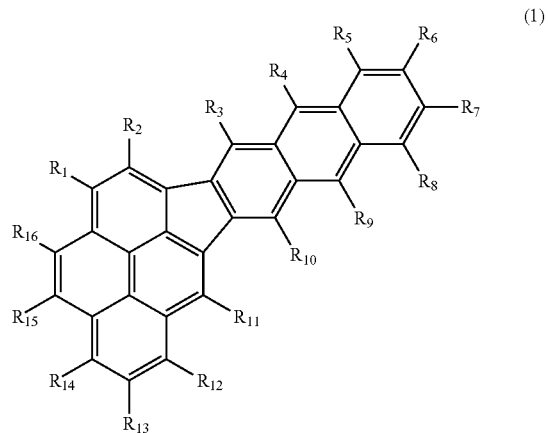

(1)

In general formula (1), $R_1$ to $R_{16}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group. At least one of $R_3$, $R_4$, $R_9$, and $R_{10}$ is selected from a substituted or unsubstituted aryl group and a substituted or unsubstituted heterocyclic group.

Aspects of the present invention provide a novel compound useful as a material, in particular, a dopant (guest material), for an organic light-emitting device. Furthermore, aspects of the present invention provide a device having high luminous efficiency and emitting light at a light quantity even if the device is driven at a low voltage.

BRIEF DESCRIPTION OF DRAWING

FIG. 1 is a schematic cross-sectional view of an organic light-emitting device and a thin-film transistor.

DESCRIPTION OF EMBODIMENTS

A compound according to aspects of the present invention will be described in detail below.

A novel compound according to aspects of the present invention is a naphtho[2',3':5,6]indeno[1,2,3-cd]pyrene derivative represented by general formula (1):

[Chem. 2]

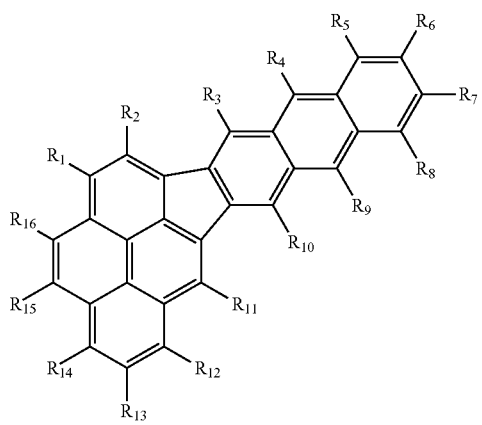

(1)

In general formula (1), $R_1$ to $R_{16}$ are each independently selected a hydrogen atom, a halogen atom, substituted or unsubstituted alkyl groups, substituted or unsubstituted alkoxy groups, substituted or unsubstituted amino groups, substituted or unsubstituted aryl groups, and substituted or unsubstituted heterocyclic groups. At least one of $R_3$, $R_4$, $R_9$, and $R_{10}$ is selected from substituted or unsubstituted aryl groups and substituted or unsubstituted heterocyclic groups.

Examples of an alkyl group in general formula (1) include, but are not limited to, methyl, ethyl, n-propyl, isopropyl, n-butyl, tert-butyl, sec-butyl, octyl, 1-adamantyl, and 2-adamantyl groups.

Examples of an alkoxy group in general formula (1) include, but are not limited to, methoxy, ethoxy, propoxy, 2-ethyl-octyloxy, phenoxy, 4-tert-butylphenoxy, benzyloxy, and thienyloxy groups.

Examples of an amino group in general formula (1) include, but are not limited to, N-methylamino, N-ethylamino, N,N-dimethylamino, N,N-diethylamino, N-methyl-N-ethylamino, N-benzylamino, N-methyl-N-benzylamino, N,N-dibenzylamino, anilino, N,N-diphenylamino, N,N-dinaphthylamino, N,N-difluorenylamino, N-phenyl-N-tolylamino, N,N-ditolylamino, N-methyl-N-phenylamino, N,N-dianisolylamino, N-mesityl-N-phenylamino, N,N-dimesitylamino, N-phenyl-N-(4-tert-butylphenyl)amino, and N-phenyl-N-(4-trifluoromethylphenyl)amino groups.

Examples of an aryl group in general formula (1) include, but are not limited to, phenyl, naphthyl, indenyl, biphenyl, terphenyl, and fluorenyl groups.

Examples of a heterocyclic group in general formula (1) include, but are not limited to, pyridyl, oxazolyl, oxadiazolyl, thiazolyl, thiadiazolyl, carbazolyl, acridinyl, and phenanthryl groups.

Examples of a substituent of each of the substituents, $R_1$ to $R_{16}$, which are selected from alkyl, alkoxy, amino, aryl, and heterocyclic groups, in general formula (1) include, but are not limited to, alkyl groups, such as methyl, ethyl, and propyl groups; aralkyl groups, such as a benzyl group; aryl groups, such as phenyl and biphenyl groups; heterocyclic groups, such as pyridyl and pyrrolyl groups; amino groups, such as dimethylamino, diethylamino, dibenzylamino, diphenylamino, and ditolylamino groups; alkoxy groups, such as methoxy, ethoxy, propoxy, and phenoxy groups; a cyano group; and halogen atoms, such as fluorine, chlorine, bromine, and iodine.

While specific examples of the compound represented by general formula (1) will be illustrated below, the present invention is not limited thereto.

[Chem. 3]

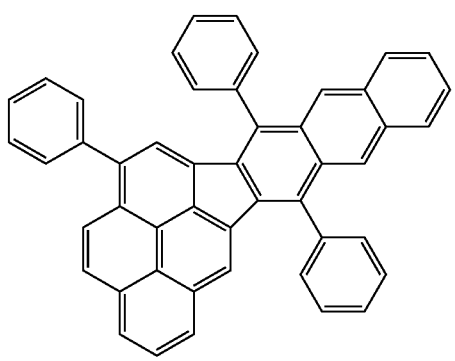

A1

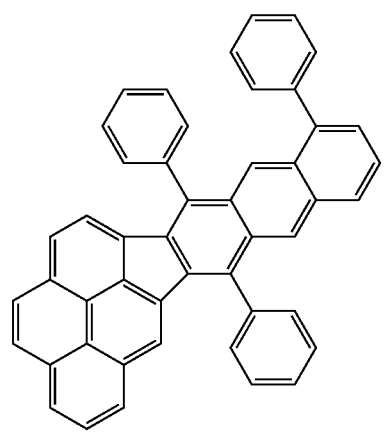

A2

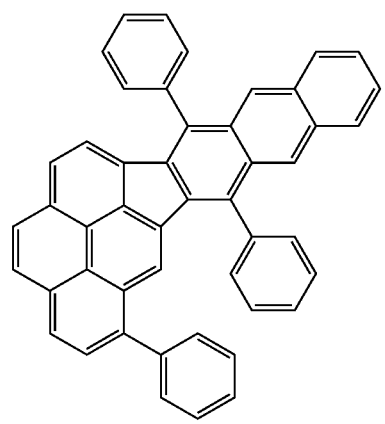

A3

-continued
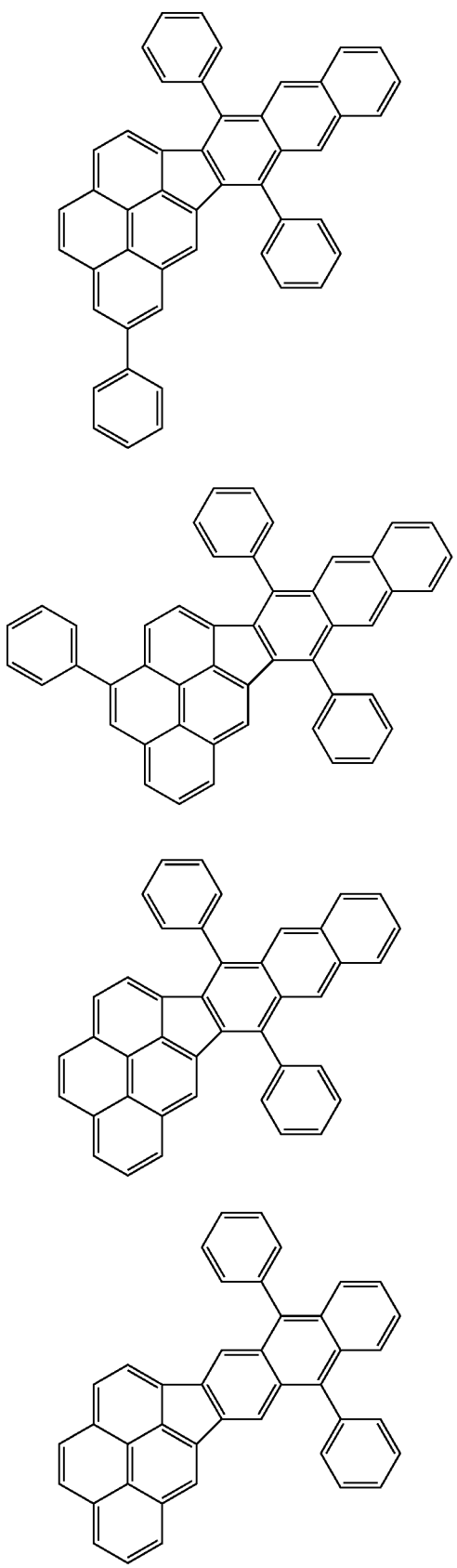
A4
A5
A6
A7
-continued
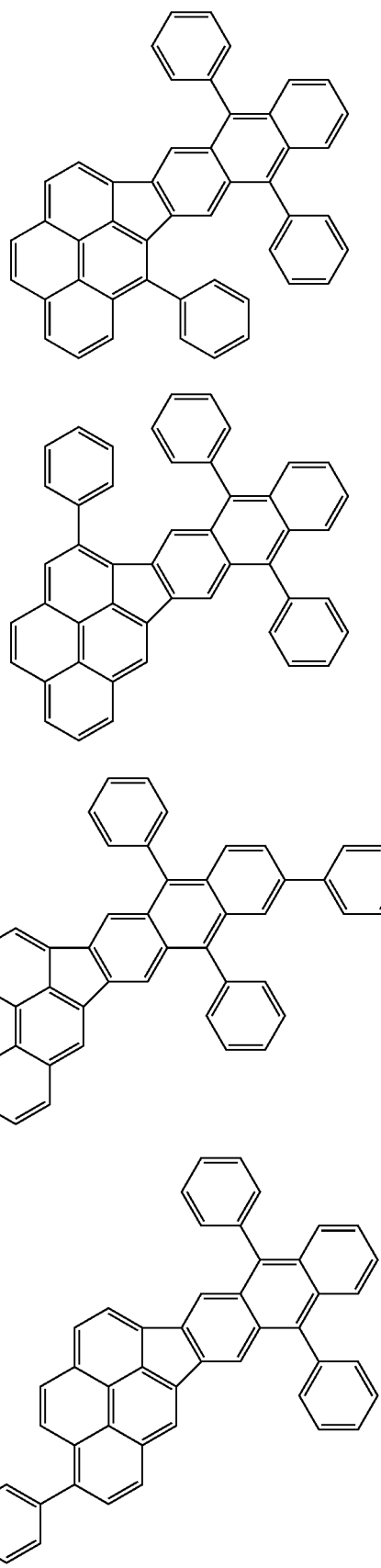
A8
A9
A10
A11

A12
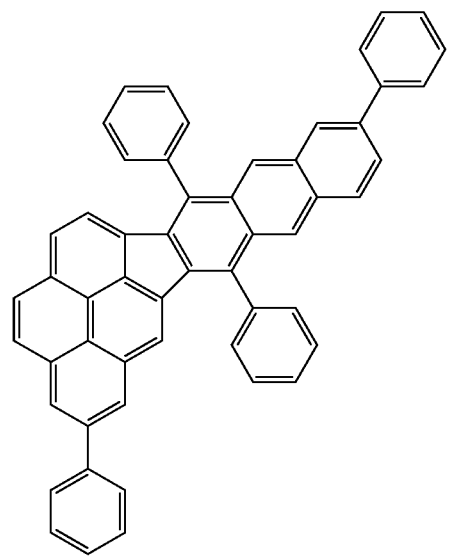
A13
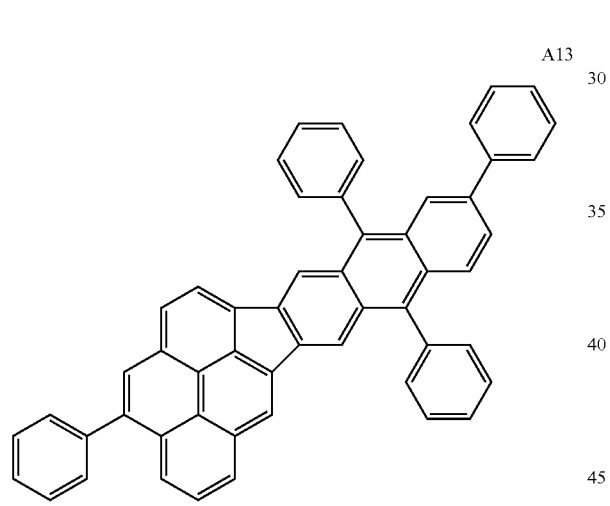
A14
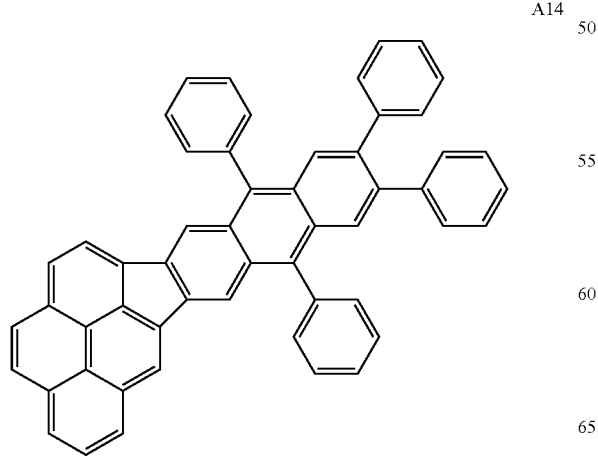
A15
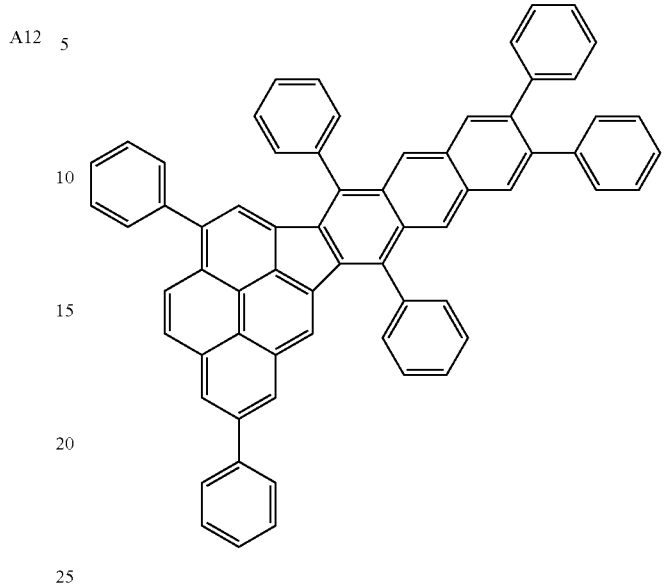
A16
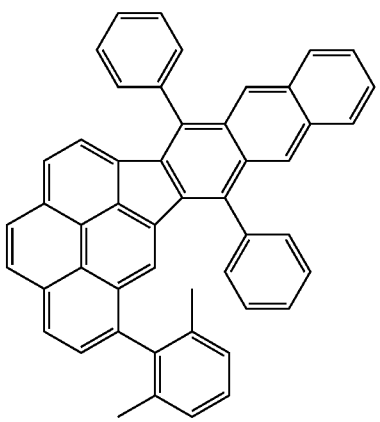
A17
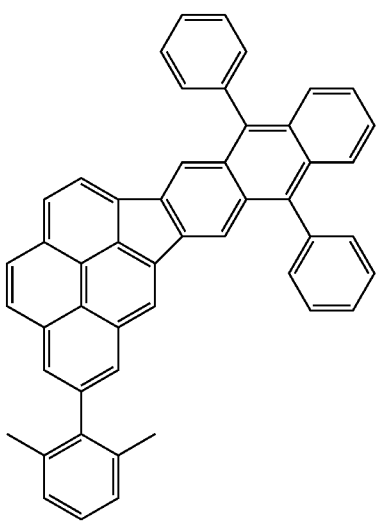

A18
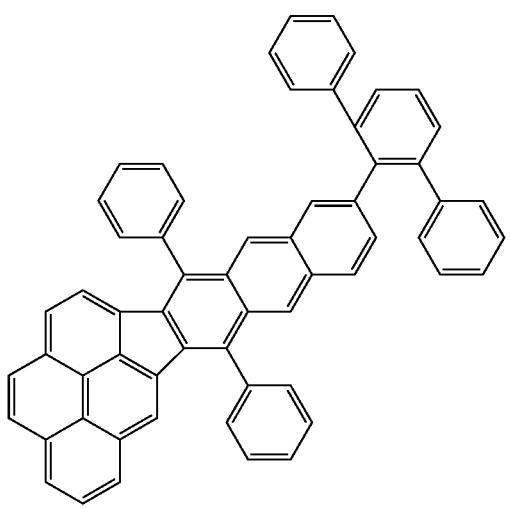
A19
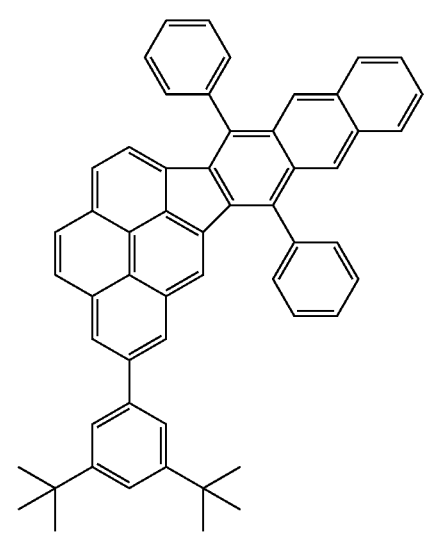
[Chem. 4]
A21
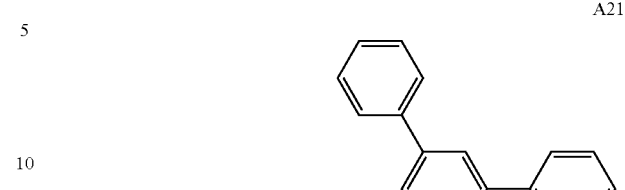
A20
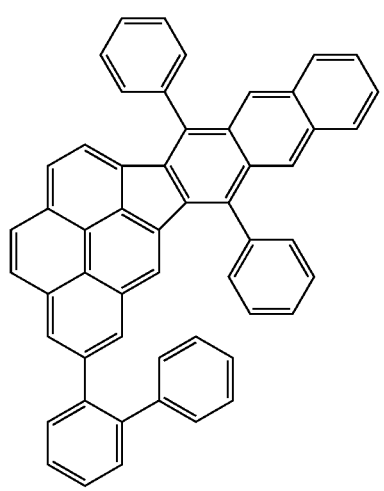
A22
A23
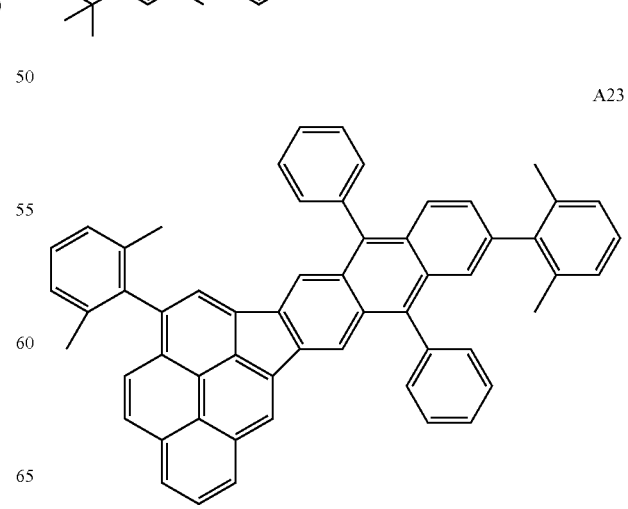

A24
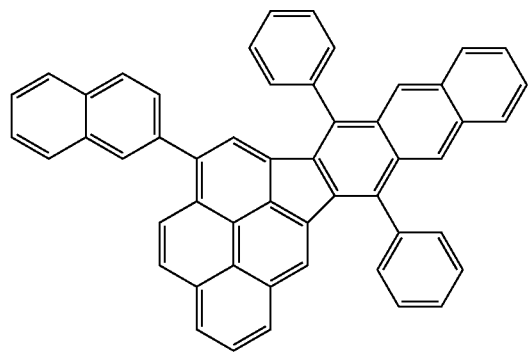
A25
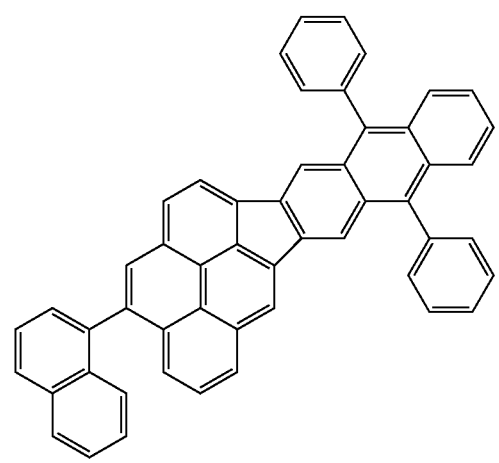
A26
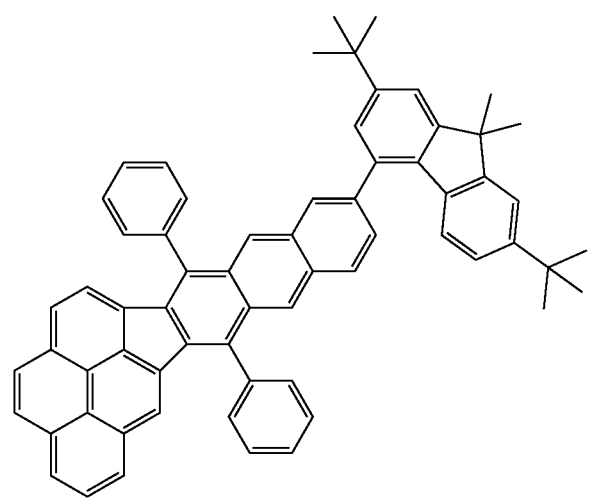
A27
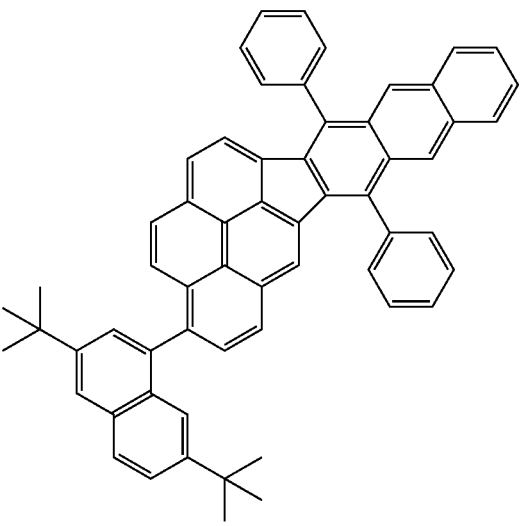
A28
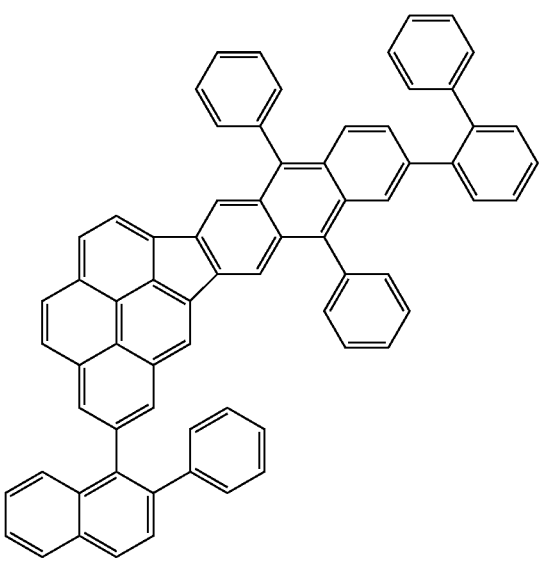
A29
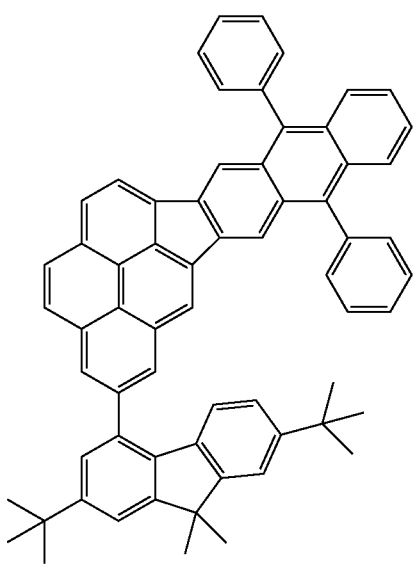

-continued
A30
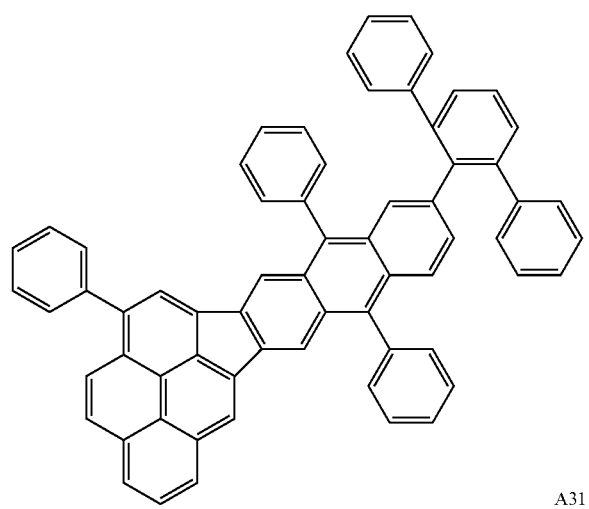
A31
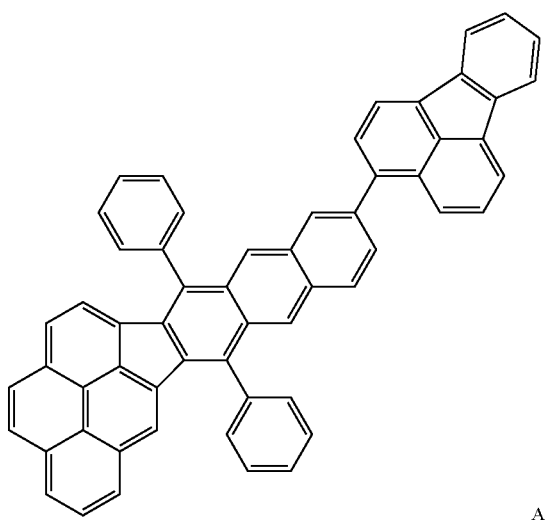
A32
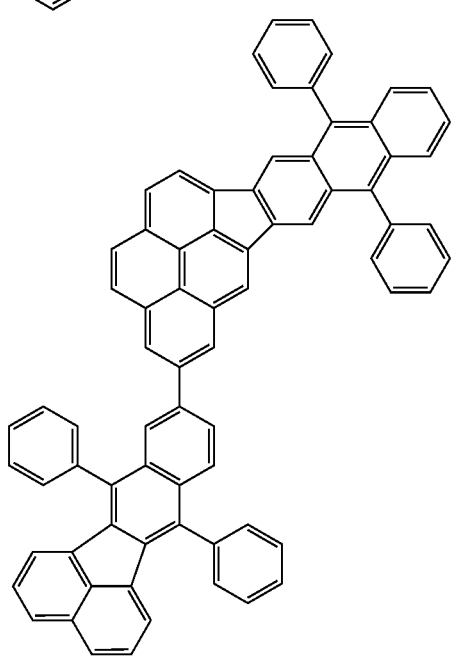
-continued
A33
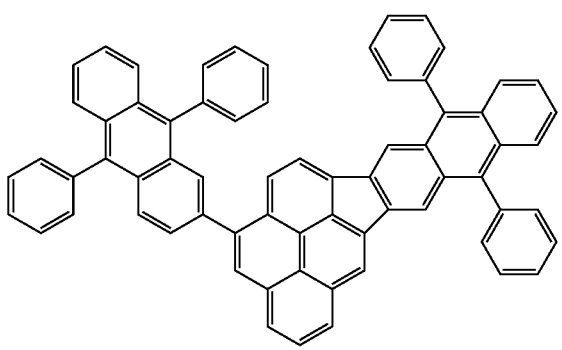
A34
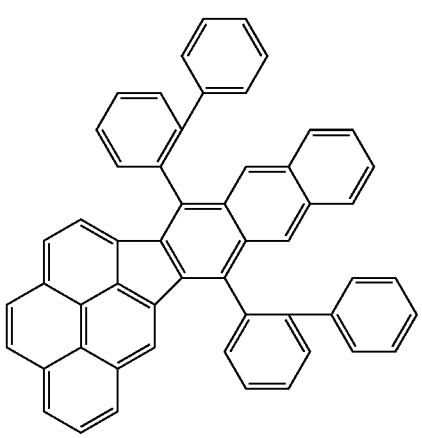
A35
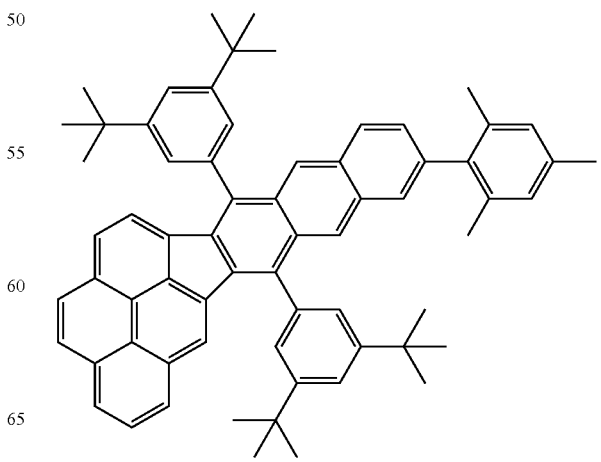

A36
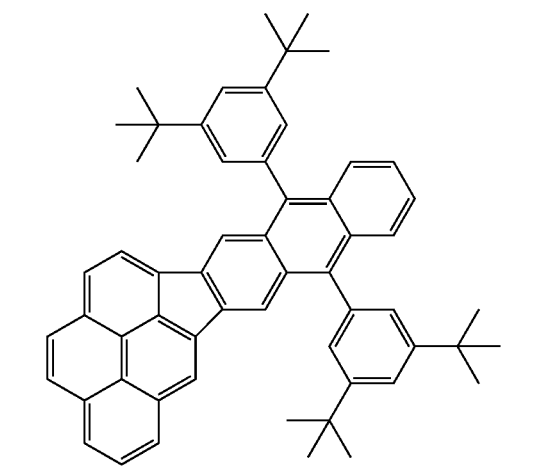
A37
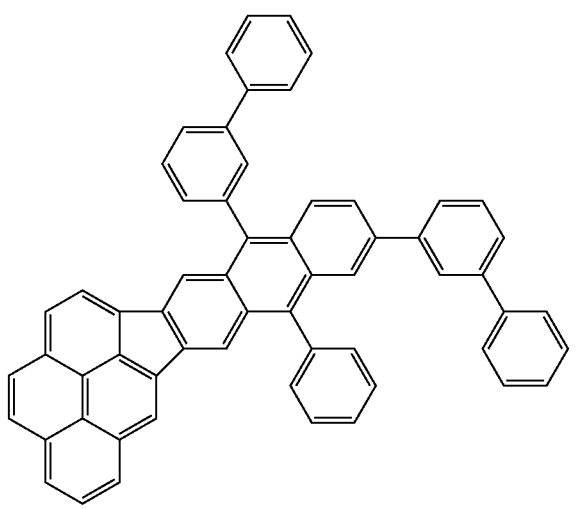
A38
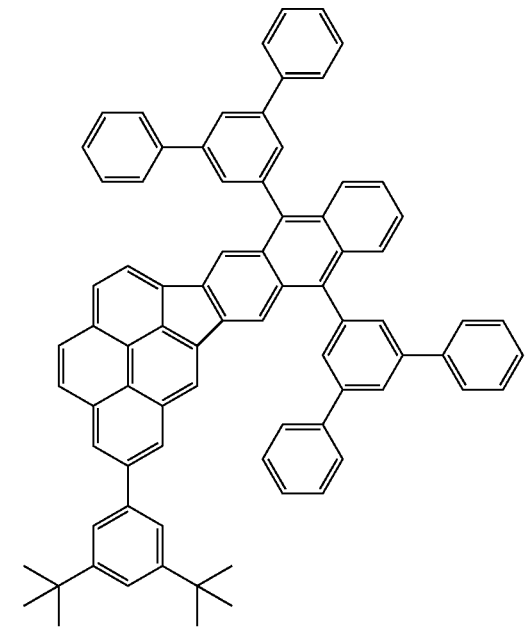
A39
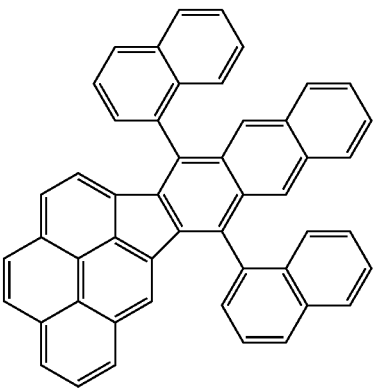
A40
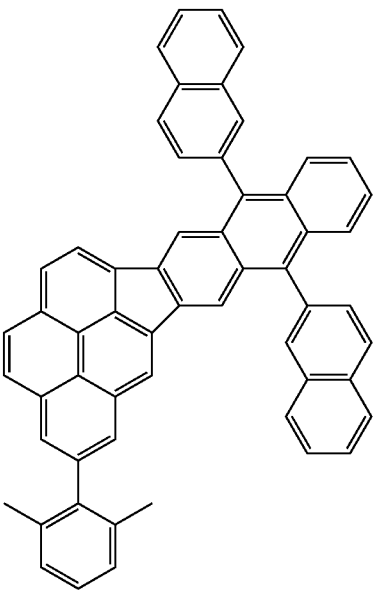
[Chem. 5]
A41
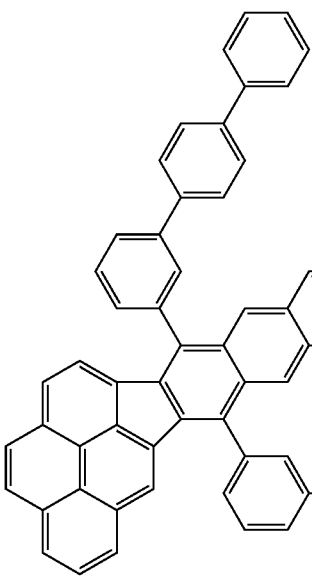

-continued
A42
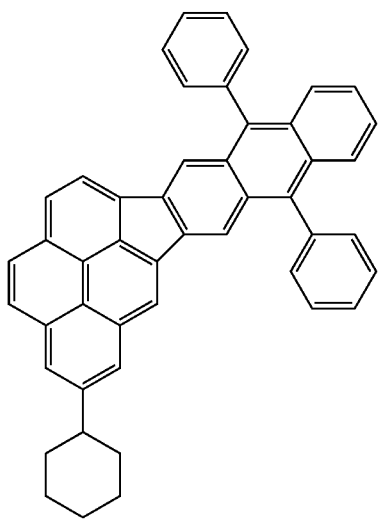
A43
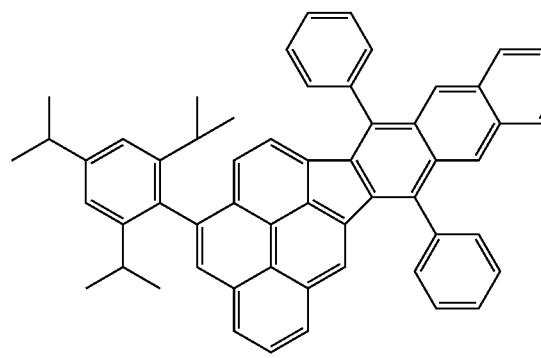
A44
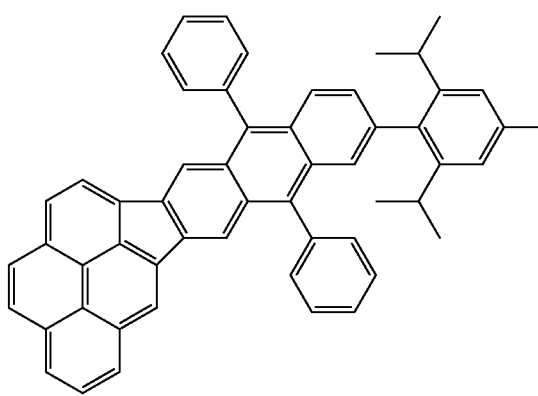
A45
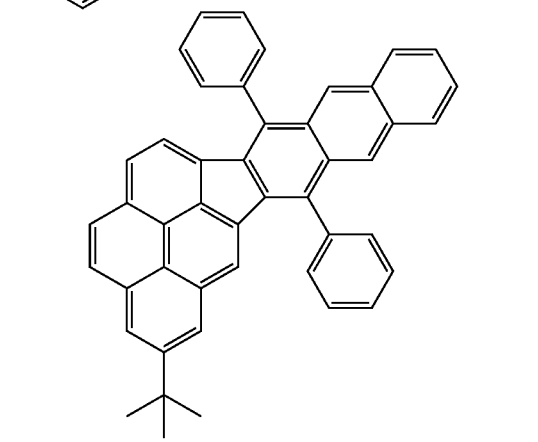
-continued
A46
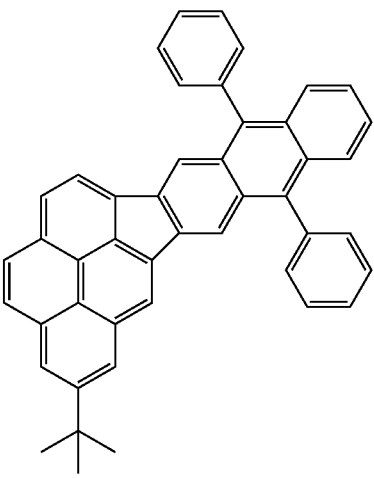
A47
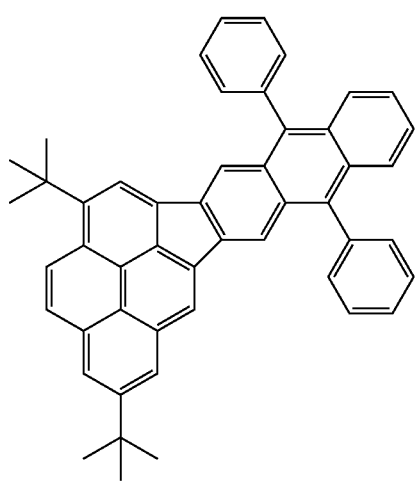
A48
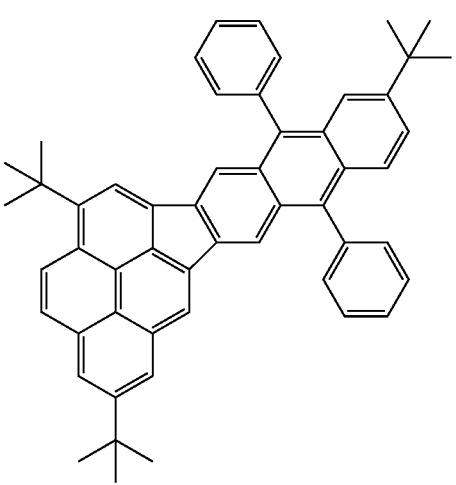

A49
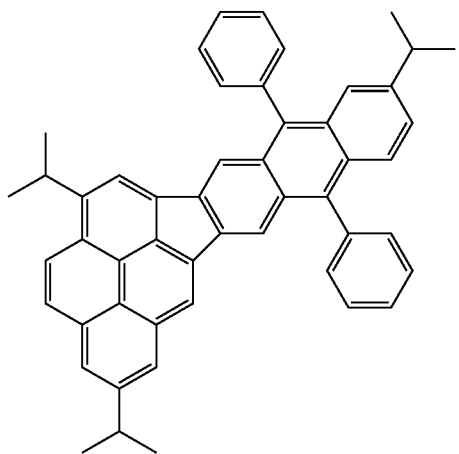
B1
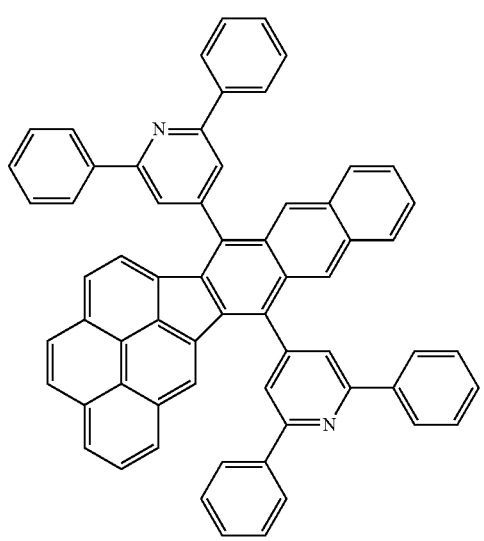
B2
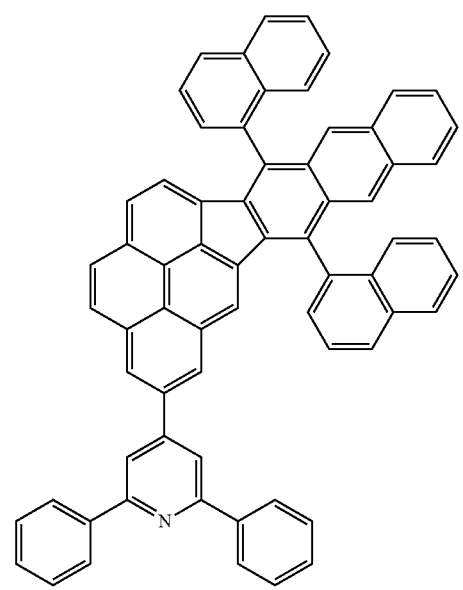
B3
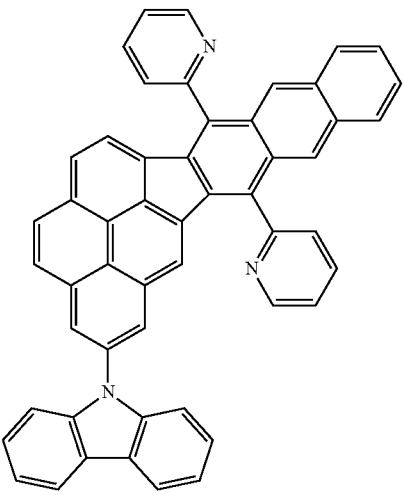
B4
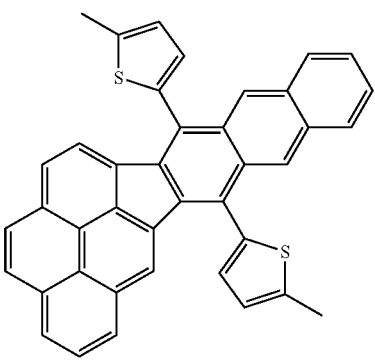
B5
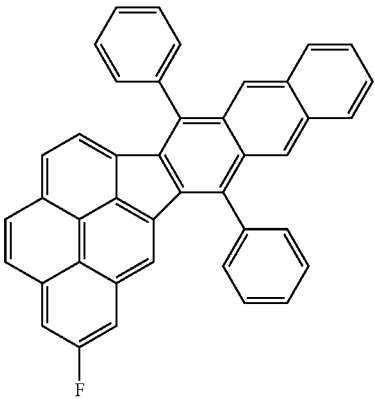

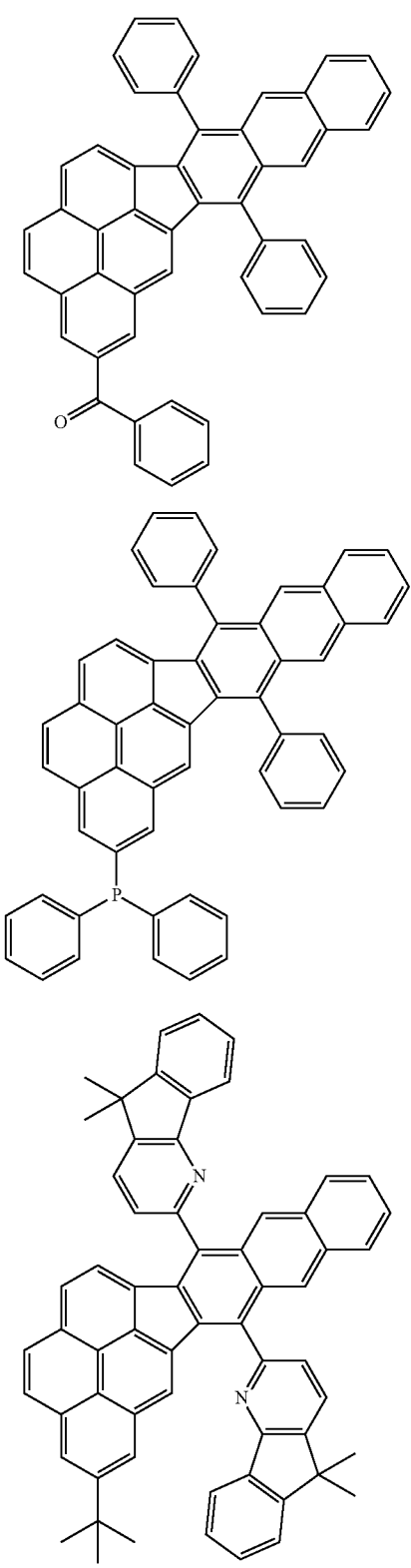

The novel organic compound according to aspects of the present invention will be described in more detail below.

To increase the luminous efficiency of an organic light-emitting device, in general, a material serving as a luminescent center can have a high emission quantum yield.

To this end, high oscillator strength and a small vibrational portion of its skeleton involved in light emission are important.

With respect to high oscillator strength, it is important to increase the symmetry of a molecular skeleton involved in light emission. Some of highly symmetric molecules emit no light under forbidden transition conditions characteristic thereof. The elongation of a conjugation sequence in a direction of the longest conjugate plane increases the dipole moment of a molecule to enhance the oscillator strength.

With respect to the small vibrational portion of a skeleton involved in light emission, the absence of a rotational structure in a skeleton prevents a reduction in quantum yield due to rotation and vibration.

The inventors have found that naphtho[2',3':5,6]indeno[1,2,3-cd]pyrene (hereinafter, referred to as a "basic skeleton") according to aspects of the present invention satisfies the requirements described above.

The basic skeleton has a fused-ring structure in which conjugation sequence extends from the 10-position to the 11-position of indeno[1,2,3-cd]pyrene. This structure leads to an increase in moment with respect to indeno[1,2,3-cd]pyrene. So, the organic compound according to aspects of the present invention has high oscillation strength. Furthermore, this basic skeleton does not have a rotational structure, thereby preventing a reduction in quantum yield.

Thus, the use of the organic compound according to aspects of the present invention increases the luminous efficiency of an organic light-emitting device.

The organic compound according to aspects of the present invention has a five-membered-ring structure in the basic skeleton and is thus characterized by a low HOMO-LUMO energy level. That is, the compound according to aspects of the present invention has a low oxidation potential. This indicates that a large amount of energy is required to oxidize the compound. So, the organic compound is stable against oxidation.

When the organic compound according to aspects of the present invention is used as a light-emitting material, the compound is also suitably used as an electron-trapping light-emitting material.

The compound according to aspects of the present invention may be used as a dopant. Dopants of the related art have problems in which a high dopant concentration causes concentration quenching and in which an excimer is formed to cause an emission wavelength to shift to longer wavelengths.

The basic skeleton of a compound according to aspects of the present invention has high planarity. If the compound having only the basic skeleton is used, concentration quenching and excimer formation are likely to occur because of intermolecular stacking. However, at least one of $R_3$, $R_4$, $R_9$, and $R_{10}$ is arranged as a substituent configured to prevent the stacking of the molecules, thereby overcoming the problem.

That is, the organic compound according to aspects of the present invention has a bulky structure as a dopant molecule. The molecule has a nonplanar structure as a whole. Intermolecular stacking is prevented by steric hindrance, thus preventing concentration quenching and excimer formation.

To elucidate this mechanism, the effect of the steric hindrance of a substituent was determined by calculation.

Specifically, the quantum chemical calculation is performed by a density functional theory at the B3LYP/6-31G* level to determine a dihedral angle between the basic skeleton and a substituent (a phenyl group in this calculation). The results demonstrate that a larger dihedral angle results in a higher effect of steric hindrance.

Table 1 shows the results. Table 1 also shows an absorption value (S1) obtained by the quantum chemical calculation.

TABLE 1

| | Structural formula | Dihedral angle (°) | Absorption value (S1) (mm) |
|---|---|---|---|
| Unsubstituted compound | | — | 454.3 |
| 1-Phenyl-substituted compound | | 55.2 | 459.0 |
| 2-Phenyl-substituted compound | | 56.1 | 460.2 |
| 3-Phenyl-substituted compound | | 89.8 | 454.5 |

TABLE 1-continued

| | Structural formula | Dihedral angle (°) | Absorption value (S1) (nm) |
|---|---|---|---|
| 4-Phenyl-substituted compound | | 79.6 | 458.4 |
| 5-Phenyl-substituted compound | | 54.3 | 459.5 |
| 6-Phenyl-substituted compound | | 37.0 | 461.6 |

TABLE 1-continued

| | Structural formula | Dihedral angle (°) | Absorption value (S1) (nm) |
|---|---|---|---|
| 7-Phenyl-substituted compound | | 37.1 | 460.2 |
| 9-Phenyl-substituted compound | | 89.8 | 458.6 |
| 10-Phenyl-substituted compound | | 89.9 | 454.6 |
| 11-Phenyl-substituted compound | | 80.2 | 458.2 |

TABLE 1-continued

| Structural formula | Dihedral angle (°) | Absorption value (S1) (nm) |
|---|---|---|
| 12-Phenyl-substituted compound | 55.9 | 465.1 |
| 13-Phenyl-substituted compound | 39.1 | 456.3 |
| 14-Phenyl-substituted compound | 54.6 | 465.9 |
| 15-Phenyl-substituted compound | 54.3 | 458.6 |

TABLE 1-continued

| Structural formula | Dihedral angle (°) | Absorption value (S1) (mm) |
|---|---|---|
| 16-Phenyl-substituted compound 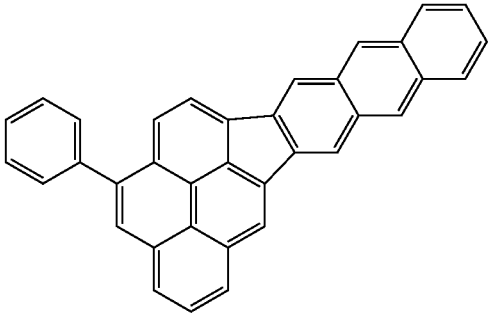 [SMILES: c1ccc(-c2cc3cccc4cc5c6c(ccc2c6c34)-c2cc3cc4ccccc4cc3cc2-5)cc1] | 55.2 | 454.7 |

The most effective positions of the substituent to prevent concentration quenching and excimer formation due to intermolecular stacking are the 3-, 4-, 9-, and 10-positions, at which large dihedral angles are provided.

At these positions, the dihedral angle is 88° or more, and the phenyl group is substantially perpendicular to the basic skeleton.

With respect to an increase in wavelength due to the spreading of the electron cloud, the conjugation sequence is less likely to extend to the substituent because of its substantially perpendicular arrangement. These substitution positions allow the electronic state of the basic skeleton to be maintained easily.

Here, examples of the substituent attached to the 3-, 4-, 9-, or 10-position include substituted or unsubstituted alkyl groups, substituted or unsubstituted amino groups, substituted or unsubstituted aryl groups, and substituted or unsubstituted heterocyclic groups. Specific examples thereof are described above.

The term "perpendicular" described above indicates that the plane of the substituent attached to the 3-, 4-, 9-, or 10-position is perpendicular to the plane of the basic skeleton.

A derivative can be used in which one of $R_3$ and $R_4$ is selected from substituted or unsubstituted aryl groups, and the other is selected from a hydrogen atom and a halogen atom, and in which one of $R_9$ and $R_{10}$ is selected from substituted or unsubstituted aryl groups, and the other is selected from a hydrogen atom and a halogen atom. The derivative has an excellent effect of preventing concentration quenching and excimer formation due to intermolecular stacking and is easily produced.

An example of a method for changing the emission wavelength of the organic compound according to aspects of the present invention into a wavelength suitable for an organic light-emitting device is a method in which a substituent is attached. In this case, absorption values (S1) at different attachment positions of an aryl group on the basic skeleton were compared. The absorption value enables us to predict a change in maximum emission wavelength. Table 1 shows the results. The results demonstrate that the attachment of the substituent to the 6-, 7-, 12-, or 14-position will result in a longer emission wavelength than the emission wavelength of an unsubstituted compound. Furthermore, the attachment of the substituent to another position permits the emission wavelength to be finely adjusted.

In the case of exemplified compounds A1 to A49 described above, substituents attached to the 1- to 8-positions and the 10- to 15-positions are selected from aryl groups and alkyl groups, and substituents attached to the 3-, 4-, 9-, and 10-positions are selected from aryl groups (in particular, phenyl group, naphthyl groups, and biphenyl groups). In this case, the emission wavelength of the substituted compound is longer than the emission wavelength of the basic skeleton. This is because the attachment of the aryl groups to these positions extends the conjugation sequence of the basic skeleton, thereby reducing the band gap of the molecule. This results in a longer emission wavelength than the emission wavelength of the unsubstituted compound (basic skeleton). Furthermore, the substituents attached to the 3-, 4-, 9-, and 10-positions are perpendicular to the basic skeleton, so that a three-dimensionally bulky structure is provided, thereby preventing intermolecular stacking and concentration quenching. All substituents are composed of hydrocarbons. When half the value of the sum of the oxidation potential and the reduction potential of the basic skeleton is defined as a center position, these organic compounds can have a changed range of the oxidation-reduction potential with the center position maintained.

For compounds, such as exemplified compounds B1 to B8, each containing a substituent having a heterostructure, such as an amino group or an aryl group having a hetero atom, the use of the heterostructure makes it possible to control the change in oxidation-reduction potential, resulting in a longer maximum emission wavelength. Furthermore, such compounds may be used as electron-trapping light-emitting materials, electron-transporting light-emitting materials, hole-transporting light-emitting materials, and hole-trapping light-emitting materials.

The naphtho[2',3':5,6]indeno[1,2,3-cd]pyrene derivative represented by general formula (1) may be synthesized by a method, for example, synthetic route 1 or 2, described below.

Synthetic Route 1

[Chem. 6]

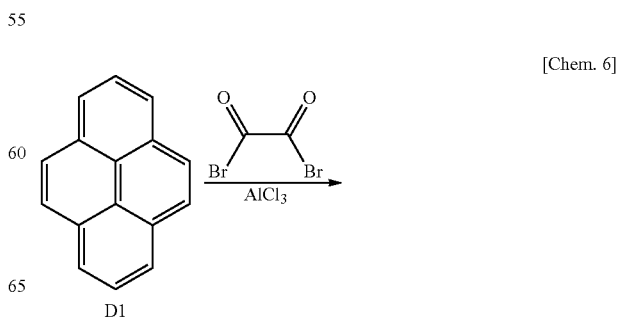

D1

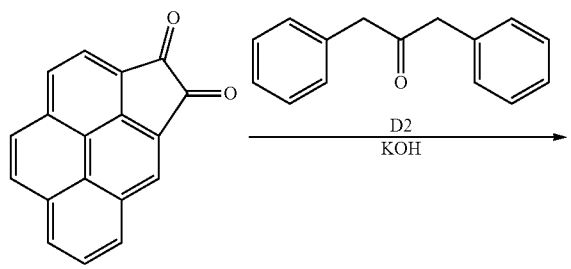

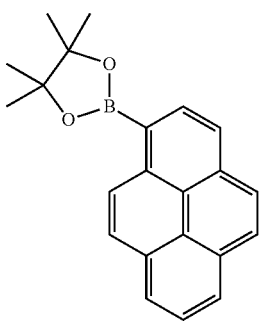

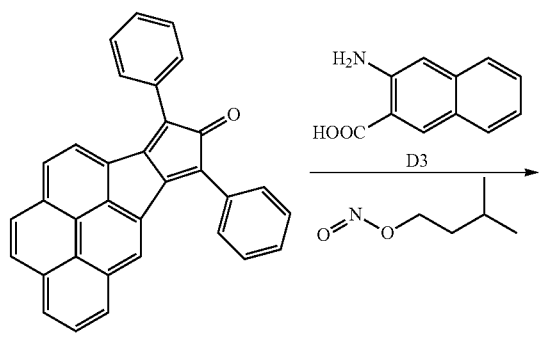

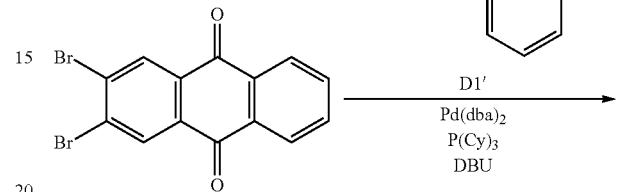

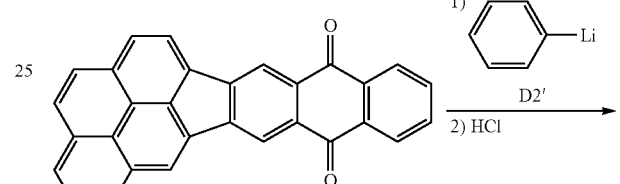

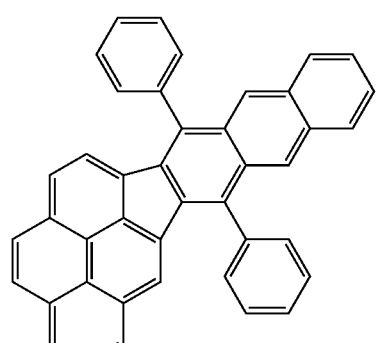

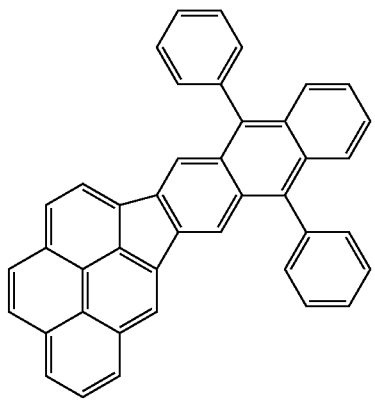

Synthetic Route 2

[Chem. 7]

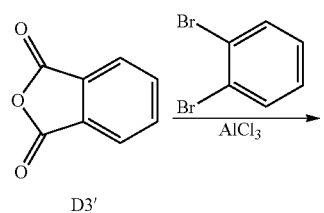

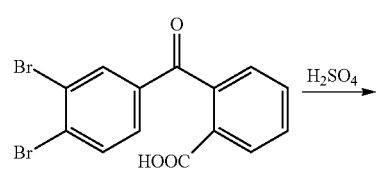

Various organic compounds according to according to aspects of the present invention may be synthesized from starting materials D1 to D3, or D1' to D3'. These syntheses can produce isomers. The isomers have substantially the same light-emitting properties. So, the isomers may be isolated by recrystallization, and then the isolated isomers may be used alone. Alternatively, the isomers may be used as a mixture. The mixing ratio is not particularly limited because the light-emitting properties of the mixture are not significantly reduced compared with those of one of the isolated isomers.

Table 2 shows various organic compounds according to aspects of the present invention synthesized from the starting materials D1 to D3 and D1' to D3'.

TABLE 2
| Synthesis | D1 (D1') | D2 (D2') | D3 (D3') | Synthetic compound | Synthetic compound No. |
|---|---|---|---|---|---|
| Synthesis Example 1 | 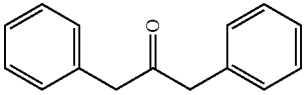 |  | 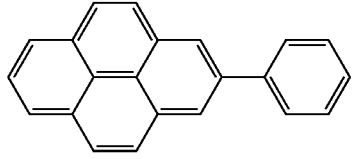 | 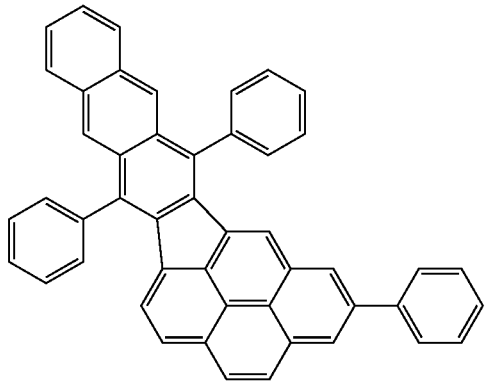 | A4 |
| Synthesis Example 2 | 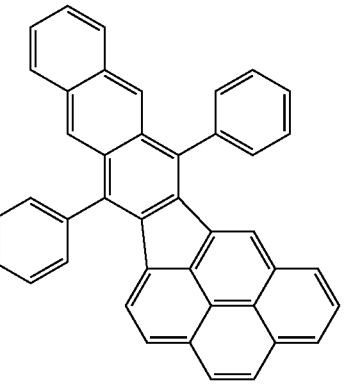 | 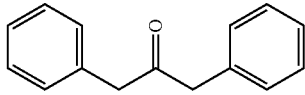 | 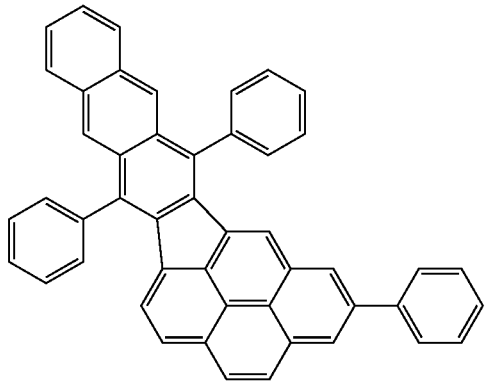 | 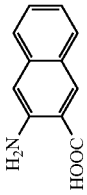 | A6 |

TABLE 2-continued

| | D1 (D1') | D2 (D2') | D3 (D3') | Synthetic compound | Synthetic compound No. |
|---|---|---|---|---|---|
| Synthesis Example 3 | pyrene-Bpin | PhLi | phthalic anhydride | | A7 |
| Synthesis Example 4 | phenylpyrene-Bpin | PhLi | phthalic anhydride | | A11 |

TABLE 2-continued
| Synthesis | D1 (D1') | D2 (D2') | D3 (D3') | Synthetic compound | Synthetic compound No. |
|---|---|---|---|---|---|
| Synthesis Example 5 | 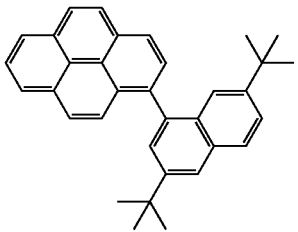 |  | 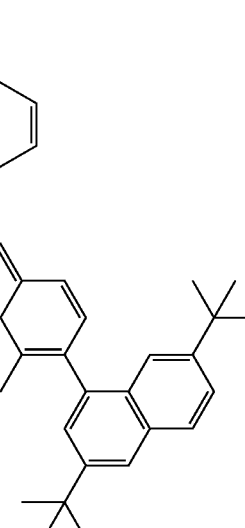 | 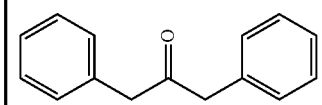 | A27 |
| Synthesis Example 6 | 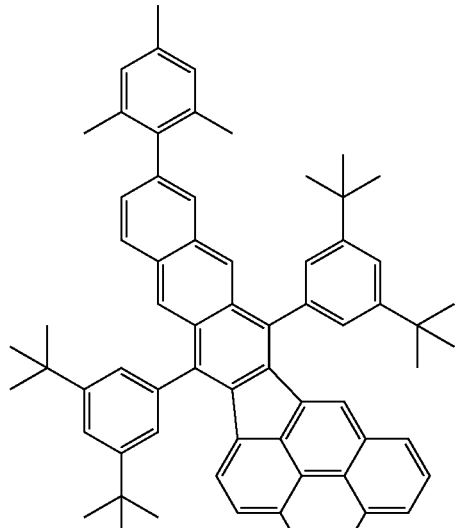 | | | | A35 |

TABLE 2-continued
| | D1 (D1') | D2 (D2') | D3 (D3') | Synthetic compound | Synthetic compound No. |
|---|---|---|---|---|---|
| Synthesis Example 7 | 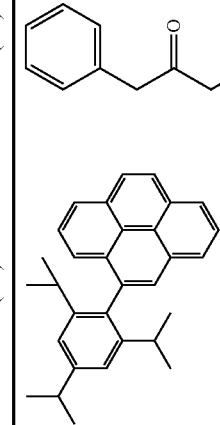 | 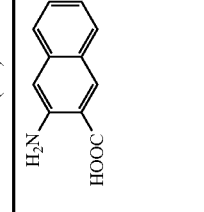 | 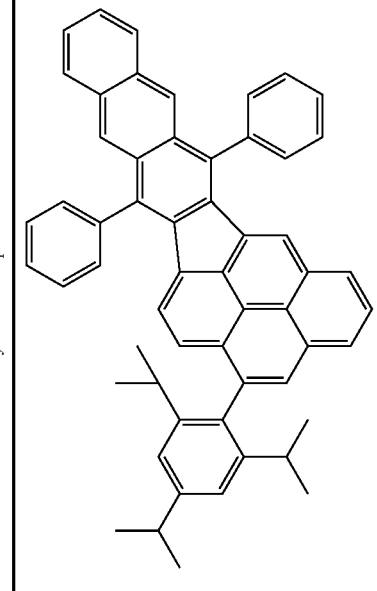 | 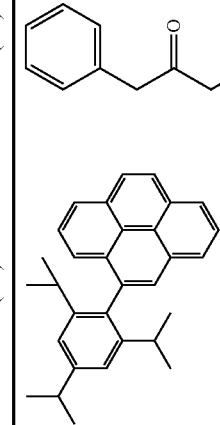 | A43 |
| Synthesis Example 8 | 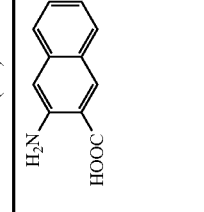 | 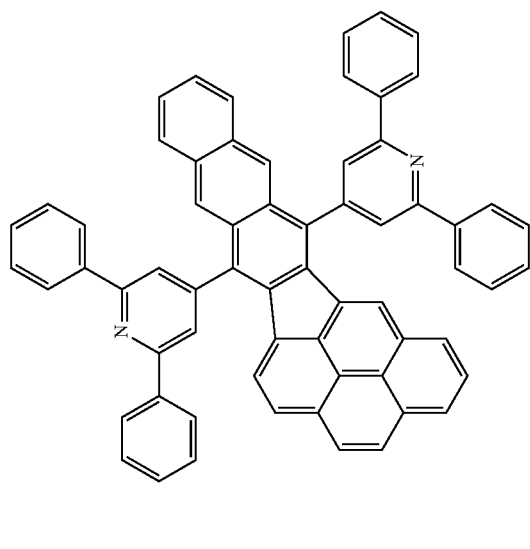 | | | B1 |

TABLE 2-continued

| Synthesis Example 9 | D1 (D1') | D2 (D2') | D3 (D3') | Synthetic compound | Synthetic compound No. |
|---|---|---|---|---|---|
| | (pyrene-PPh₂ structure) | 1,3-diphenylacetone | 3-amino-2-naphthoic acid | (fused polycyclic aromatic with two phenyl groups and PPh₂) | B7 |

An organic light-emitting device according to aspects of the present invention will be described below.

The organic light-emitting device according to aspects of the present invention includes an organic compound layer provided between an anode and a cathode, which are a pair of electrodes. The organic compound layer may be a single layer. Alternatively, the organic compound layer may be formed of functional layers, such as a hole injection layer, a hole transport layer, a light-emitting layer, an electron transport layer, an electron injection layer, a hole-blocking layer, and an electron-blocking layer (the latter is referred to as a "multilayer organic light-emitting device").

The layer contains at least one material. In the case where the layer contains a plurality of materials, the materials may be evenly or unevenly distributed in the layer distributed.

In the case where one of the organic compound layers is a light-emitting layer, it is essential that the light-emitting layer partially contain the organic compound according to aspects of the present invention and that the organic compound according to aspects of the present invention serve as an auxiliary component of the light-emitting layer.

Herein, among all compounds constituting the light-emitting layer, a main component is defined as a component contained in a large amount in terms of weight or the number of moles in terms of, for example, weight or the number of moles, and the auxiliary component is defined as a component contained in a small amount.

A material used as the main component may also be referred to as a "host material".

A material used as the auxiliary component may also be referred to as a "dopant (guest) material", an "emission assist material", or a "charge injection material".

The concentration of the organic compound according to aspects of the present invention is preferably in the range of 0.01% by weight to 20% by weight and more preferably 0.5% by weight to 10% by weight with respect to the host material. A change in the concentration of the organic compound according to aspects of the present invention within any of the two ranges described above enables the wavelength of light emitted from the light-emitting layer to be increased by 5 nm to 20 nm with respect to the wavelength of a solution. Furthermore, a plurality of the organic compounds according to aspects of the present invention may be contained. Even in this case, it is essential that all the organic compounds according to aspects of the present invention serve as auxiliary components. When the plural organic compounds according to aspects of the present invention are contained, at least one of the organic compounds may be used as an assist dopant.

First to fifth examples of a multilayer organic light-emitting device will be described below.

The first example of the multilayer organic light-emitting device has an (anode/light-emitting layer/cathode) structure, the anode, the light-emitting layer, and the cathode being provided in that order on a substrate. The organic light-emitting device used here is useful when a material having hole transport properties, electron transport properties, and light-emitting properties by itself is used in the light-emitting layer or when compounds having respective properties are used as a mixture in the light-emitting layer. The symbol "/" indicates that both sides of "/" are adjacent layers.

The second example of the multilayer organic light-emitting device has an (anode/hole transport layer/electron transport layer/cathode) structure, the anode, the hole transport layer, the electron transport layer, and the cathode being provided in that order on a substrate. In the second example, the multilayer organic light-emitting device is useful when a light-emitting material having hole transport properties and a light-emitting material having electron transport properties are used in the corresponding layers or when a light-emitting material having both properties is used in both the hole transport layer and the electron transport layer, a simple hole transport substance or electron transport substance that does not emit light being used in combination with the light-emitting material. In this case, the hole-transport layer or the electron transport layer serves as a light-emitting layer.

The third example of the multilayer organic light-emitting device has an (anode/hole transport layer/light-emitting layer/electron transport layer/cathode) structure, the anode, the hole transport layer, the light-emitting layer, the electron transport layer, and the cathode being provided in that order on a substrate. This is a device in which functions of carrier transportation and light emission are separated from each other. A light-emitting material may be used in combination with compounds having hole transport properties, electron transport properties, and light-emitting properties, as needed. Flexibility in the choice of materials is significantly increased, and various compounds having different emission wavelengths may be used. So, the variety of emission hues can be increased. In addition, carriers or excitons can be effectively confined in the central light-emitting layer to improve the luminous efficiency.

The fourth example of the multilayer organic light-emitting device has an (anode/hole injection layer/hole transport layer/light-emitting layer/electron transport layer/cathode) structure, the anode, the hole injection layer, the hole transport layer, the light-emitting layer, the electron transport layer, and the cathode being provided in that order on a substrate. This structure has the effect of improving the adhesion between the anode and the hole transport layer or improving the hole injection properties, thereby contributing to a reduction in voltage.

The fifth example of the multilayer organic light-emitting device has an (anode/hole transport layer/light-emitting layer/hole-exciton-blocking layer/electron transport layer/cathode) structure, the anode, the hole transport layer, the light-emitting layer, the hole-exciton-blocking layer, the electron transport layer, and the cathode being provided in that order on a substrate. In this structure, the layer (hole-exciton-blocking layer) that prevents the transfer of holes or excitons toward the cathode is arranged between the light-emitting layer and the electron transport layer. This structure is effective in improving the luminous efficiency by the use of a compound having a significantly high ionization potential in the hole/exciton-blocking layer.

However, the multilayer structures of the first to fifth examples are merely basic structures of organic light-emitting devices. The structure of an organic light-emitting device according to aspects of the present invention is not limited thereto. The organic light-emitting device may have various other layer structures: For example, an insulating layer may be provided between an electrode and an organic layer. An adhesive layer or an interference layer may be provided. The electron transport layer or the hole transport layer may be composed of two layers having different ionization potentials.

The compound represented by general formula (1) used in aspects of the present invention may be used in any of the first to fifth examples.

In addition to the organic compound according to aspects of the present invention, for example, low- or high-molecular weight hole transport compounds, light-emitting compounds, and electron transport compounds may be used in combination, as needed. Examples of these compounds are described below.

As a hole injection/transport material, a material having a high hole mobility can be used, so that holes can be easily injected from an anode and the injected holes can be transported to a light-emitting layer. Examples of low- and high-molecular weight materials having hole injection-transport properties include, but are not limited to, triarylamine derivatives, phenylenediamine derivatives, stilbene derivatives, phthalocyanine derivatives, porphyrin derivatives, poly(vinylcarbazole), poly(thiophene), and other electrically conductive polymers.

Examples of host materials mainly include, but are not limited to, compounds illustrated in Table 3 and their derivatives; fused ring compounds, such as fluorene derivatives, naphthalene derivatives, anthracene derivatives, pyrene derivatives, carbazole derivatives, quinoxaline derivatives, and quinoline derivatives; organoaluminum complexes, such as tris(8-quinolinolato)aluminum; organozinc complexes; and polymer derivatives, such as triphenylamine derivatives, poly(fluorene) derivatives, and poly(phenylene) derivatives.

TABLE 3

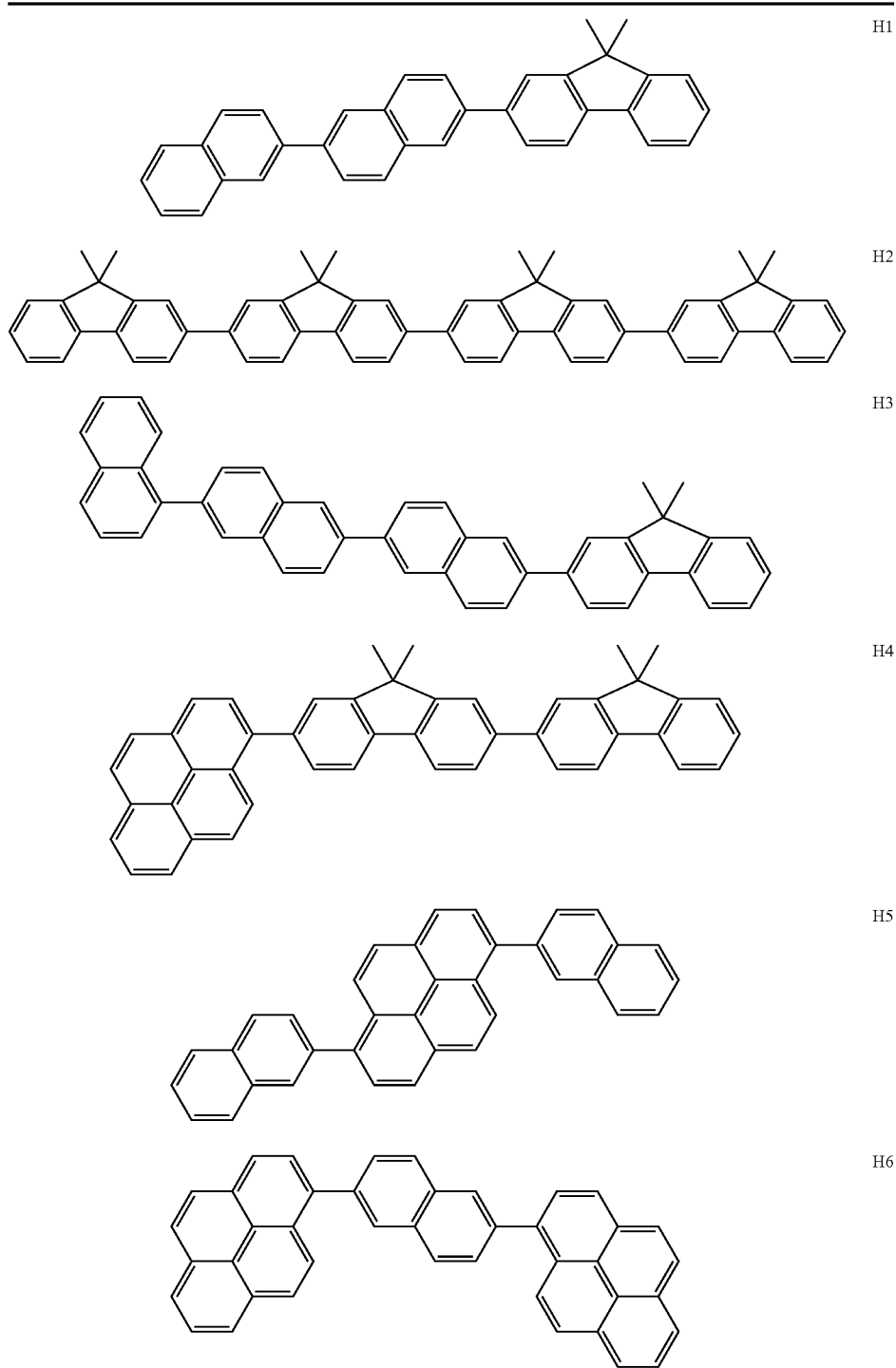

TABLE 3-continued
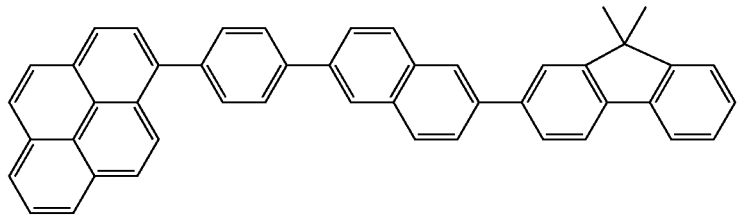 [SMILES: CC1(C)c2ccccc2-c2ccc(-c3ccc4cc(-c5ccc(-c6ccc7ccc8cccc9ccc6c7c89)cc5)ccc4c3)cc21]
H7
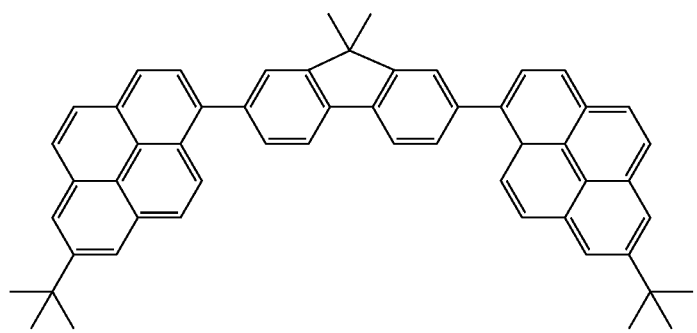
H8
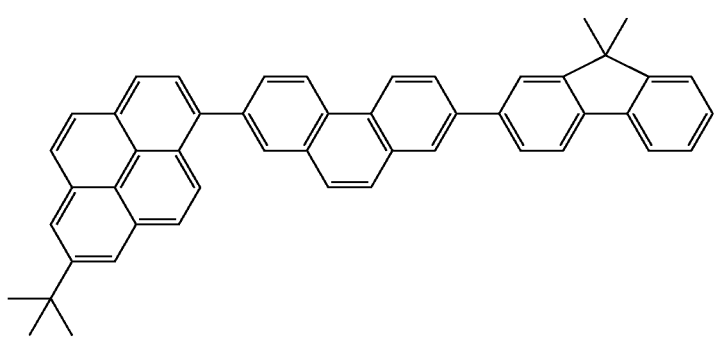 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
H9
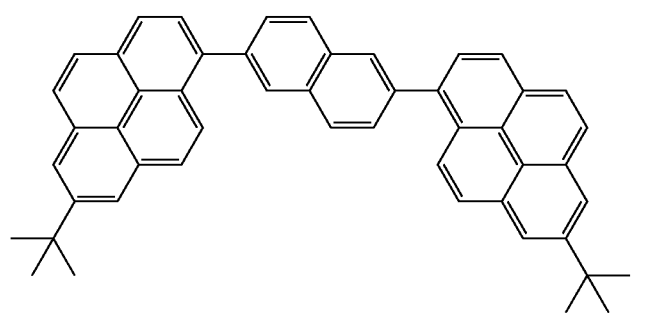 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
H10
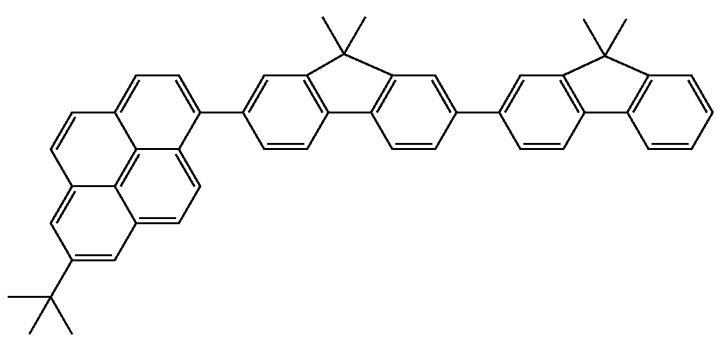 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]
H11

TABLE 3-continued
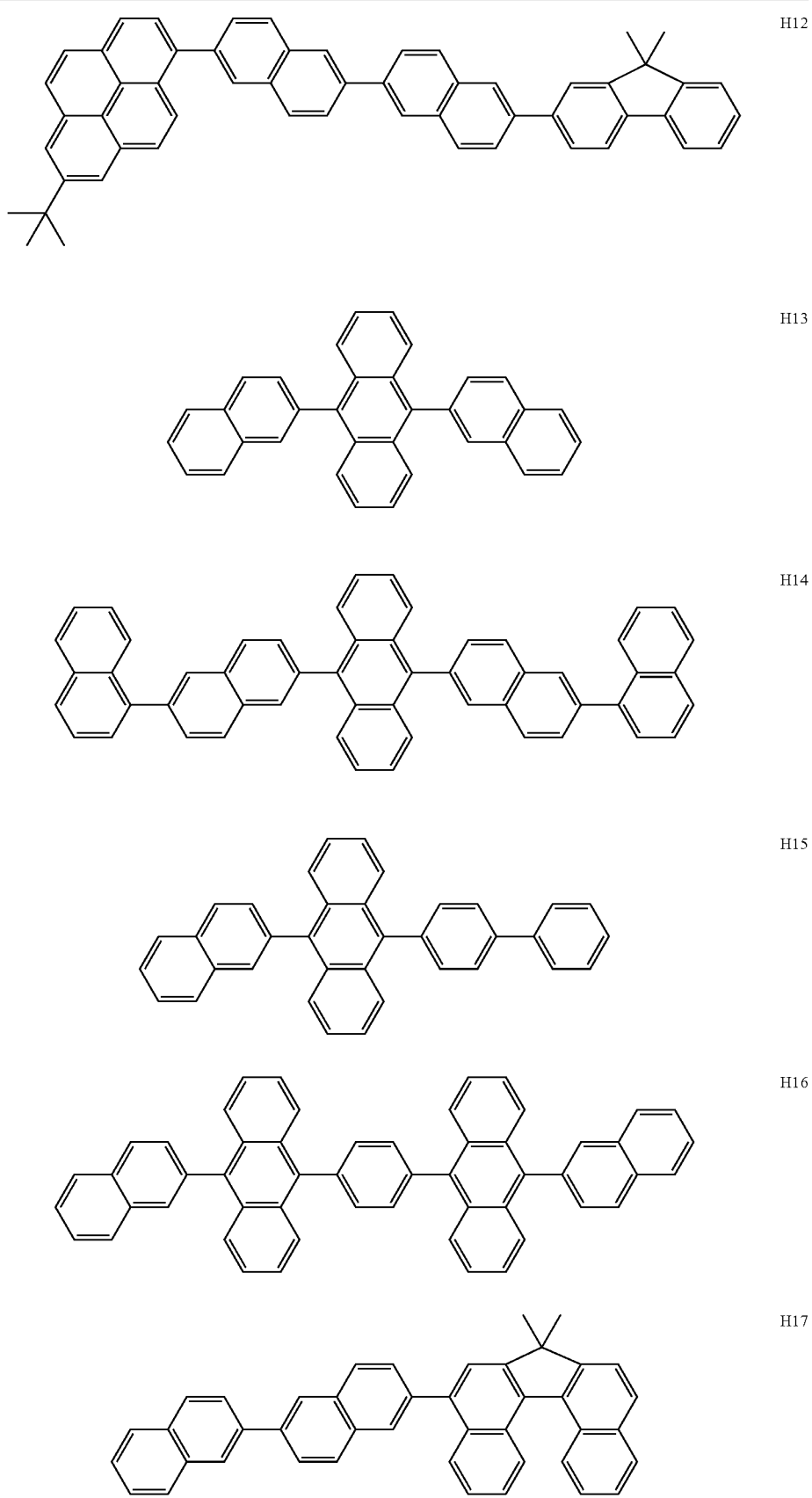
H12
H13
H14
H15
H16
H17

TABLE 3-continued
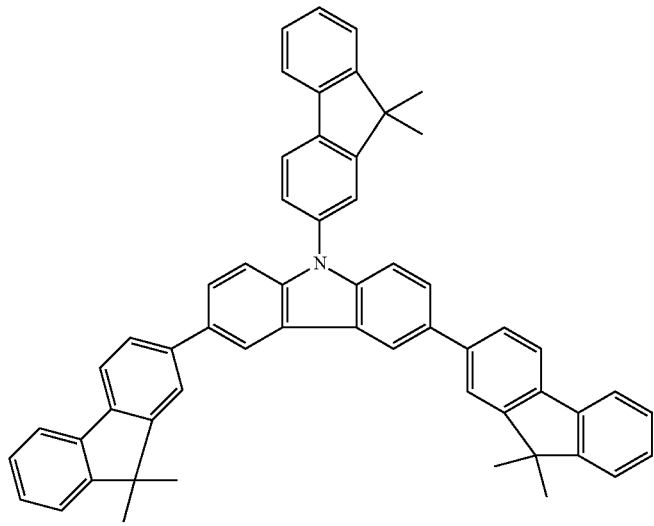 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H18
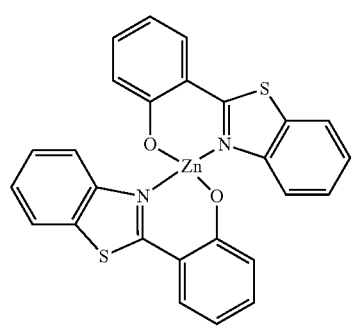
H19
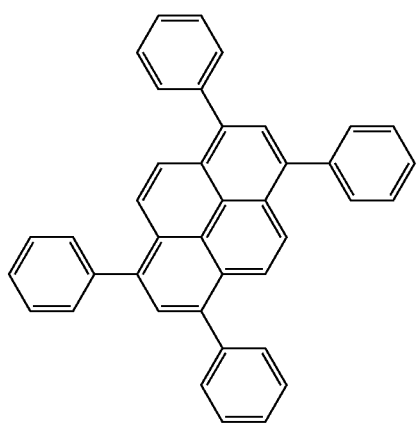 [SMILES: c1ccc(-c2cc(-c3ccccc3)c3ccc4c(-c5ccccc5)cc(-c5ccccc5)c5ccc2c3c54)cc1]
H20
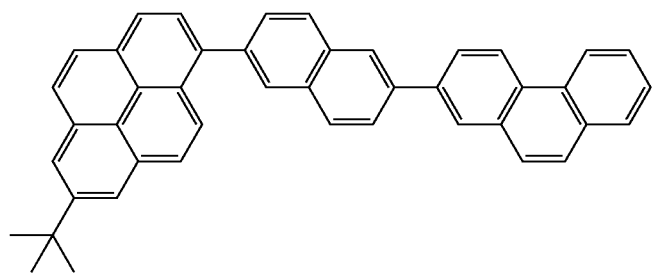 [SMILES: CC(C)(C)c1cc2ccc3ccc(-c4ccc5cc(-c6ccc7c(ccc8ccccc87)c6)ccc5c4)c4ccc(c1)c2c34]
H21

TABLE 3-continued
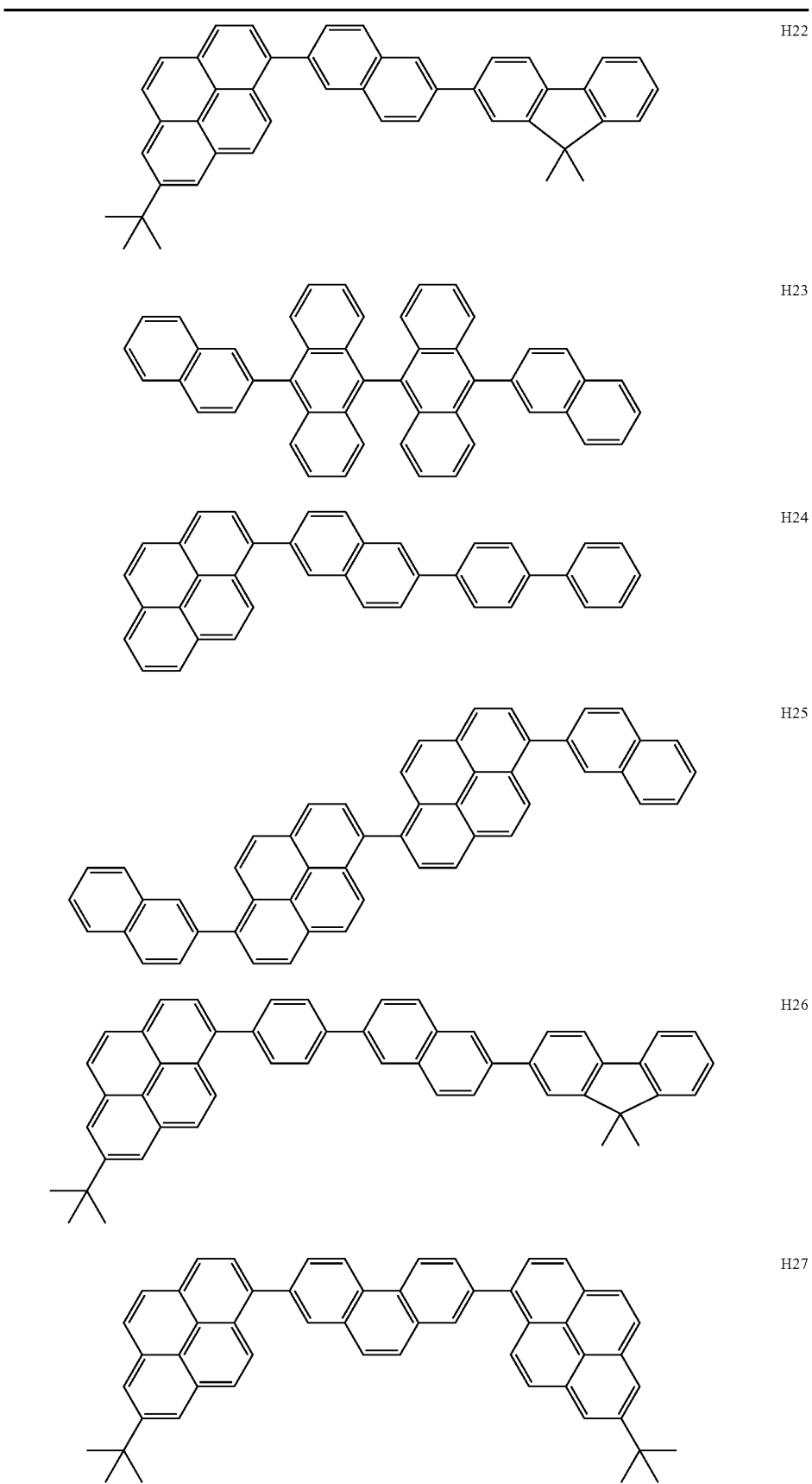
H22
H23
H24
H25
H26
H27

TABLE 3-continued

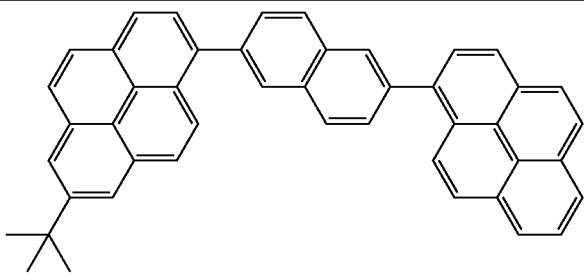

H28

As an electron injection-transport material, any material to which electrons can be easily injected from a cathode and which can transport the injected electrons to a light-emitting layer may be used. The electron injection-transport material is selected in view of, for example, the hole mobility of the hole injection/transport material. Examples of a material having the electron injection-transport properties include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

A material used for an anode can have a higher work function. Examples of the material that can be used include elemental metals, such as gold, platinum, silver, copper, nickel, palladium, cobalt, selenium, vanadium, and tungsten; alloys thereof; and metal oxides, such as tin oxide, zinc oxide, indium oxide, indium tin oxide (ITO), and indium zinc oxide. Furthermore, conductive polymers, such as polyaniline, polypyrrole, and polythiophene, may be used. These materials for the electrode may be used alone or in combination. The anode may have a single-layer structure or multilayer structure.

A material used for a cathode can have a lower work function. Examples of the material include elemental metals, such as alkali metals, e.g., lithium, alkaline-earth meals, e.g., calcium, and aluminum, titanium, manganese, silver, lead, and chromium; and alloys thereof. Examples of the alloys that can be used include magnesium-silver, aluminum-lithium, and aluminum-magnesium. Metal oxides such as indium tin oxide (ITO) may be used. These materials for the electrode may be used alone or in combination. The cathode may have a single-layer structure or multilayer structure.

Examples of a substrate for use in the organic light-emitting device according to aspects of the present invention include, but are not particularly limited to, opaque substrates, such as metal substrates and ceramic substrates; and transparent substrates, such as glass substrates, quartz substrates, and plastic sheets. Furthermore, it is possible to control the emission color using a color filter film, a fluorescent color conversion filter film, a dielectric reflection film, or the like on the substrate.

In order to prevent contact with oxygen, water, and so forth, a protective layer or a sealing layer may be arranged on the resulting organic light-emitting device. Examples of the protective layer include diamond thin films; inorganic material films composed of, for example, metal oxides and metal nitrides; and polymeric films composed of, for example, fluorinated resins, polyethylene, silicone resins, and polystyrene resins, and photocurable resins. Furthermore, the organic light-emitting device may be covered with, for example, glass, a gas-impermeable film, or a metal, and packaged in an appropriate sealing resin.

In the organic light-emitting device according to aspects of the present invention, an organic compound layer may be usually formed by a method described below. In general, a thin organic compound layer may be formed by vacuum evaporation, ionized evaporation, sputtering, or a method using plasma. Alternatively, a thin organic compound layer may be formed by a known coating method, e.g., spin coating, dipping, casting, the Langmuir-Blodgett (LB) technique, or an ink-jet method, using a solution of a material dissolved in an appropriate solvent. Here, the formation of the layer by, for example, vacuum evaporation or the coating method, is less likely to cause crystallization or the like, resulting in excellent stability with time. Furthermore, in the case of forming the layer by a coating method, the layer may be formed in combination with an appropriate binder resin.

Examples of the binder resin include, but are not limited to, polyvinylcarbazole resins, polycarbonate resins, polyester resins, acrylonitrile-butadiene-styrene (ABS) resins, acrylic resins, polyimide resins, phenolic resins, epoxy resins, silicone resins, and urea resins. These binder resins may be used alone in the form of a homopolymer or copolymer. Alternatively, these binder resins may be used in combination as a mixture. In addition, known additives, such as a plasticizer, an antioxidant, and an ultraviolet absorber, may be used in combination, as needed.

The organic light-emitting device according to aspects of the present invention can be used in products that are required to have low power consumption and high luminance. Application examples thereof include light sources for use in display apparatuses, illuminating apparatuses, and printers, and backlights for use in liquid crystal display.

When the organic light-emitting device is used for a display apparatus, it is possible to produce an energy-saving, high-legibility, lightweight flat panel display. The display apparatus may be used as an image display apparatus for a personal computer, a television set, or an advertizing medium. Alternatively, the display apparatus may be used in a display unit of an image pickup apparatus, e.g., a digital still camera or a digital video camera.

Alternatively, the display apparatus may be used in an operation display unit of an electrophotographic image-forming apparatus, e.g., a laser beam printer or a copier.

Furthermore, the organic light-emitting device according to aspects of the present invention may be used as a light source configured to expose a latent image on a photosensitive member of an electrophotographic image-forming apparatus, e.g., a laser beam printer or a copier. A plurality of organic light-emitting devices that can be independently addressed may be arranged in the form of an array (for example, lines). A predetermined exposure may be performed on a photosensitive drum to form a latent image. The use of the organic light-emitting device according to aspects of the present invention reduces the space that has been previously required to arrange polygon mirrors, various optical lenses, and other components.

The use of the device according to aspects of the present invention for lighting apparatuses and backlights provides an energy conservation effect. The organic light-emitting device according to aspects of the present invention may also be used as a flat surface light source.

To control the emission color, a color filter film, a fluorescent color conversion filter film, a dielectric reflection film, or the like may be arranged on the substrate configured to support the organic light-emitting device according to aspects of the present invention. A thin-film transistor (TFT) may be provided on the substrate and connected to the organic light-emitting device to control the emission and non-emission states. A plurality of organic light-emitting devices may be arranged in a matrix, i.e., in an in-plane direction, and used as an illuminating apparatus.

A display apparatus including the organic light-emitting device according to aspects of the present invention will be described below. The display apparatus includes the organic light-emitting device according to aspects of the present invention and a unit configured to feed an electric signal to the organic light-emitting device according to aspects of the present invention. The display apparatus according to aspects of the present invention will be described below in detail with reference to the attacked drawing by taking an active matrix system as an example.

FIG. 1 is a schematic cross-sectional view illustrating an image display apparatus according to aspects of the present invention. The structure will be described in detail below with an example of a production process of a TFT substrate.

To produce a display apparatus 1 illustrated in FIG. 1, first, a moisture-proof film 12 configured to protect components (TFTs and an organic layer) to be formed thereon is formed on a substrate 11 composed of, for example, glass. Examples of a material constituting the moisture-proof film 12 include silicon oxide; and composite materials of silicon oxide and silicon nitride. A metal film composed of, for example, Cr is formed by sputtering. The metal film is patterned to form a predetermined circuit pattern, thereby providing gate electrodes 13.

Subsequently, for example, a silicon oxide film is formed by, for example, plasma-enhanced chemical vapor deposition (CVD) or catalytic chemical vapor deposition, and then is patterned to form gate insulating films 14. Next, a silicon film is formed by, for example, plasma-enhanced CVD (and optionally annealing the silicon film at 290° C. or higher). The silicon film is patterned according to the circuit pattern, thereby providing semiconductor layers 15.

Drain electrodes 16 and source electrodes 17 are formed on the semiconductor layers 15 to provide TFT elements 18, thereby resulting in a circuit as illustrated in FIG. 1. An insulating film 19 is formed on the TFT elements 18. Contact holes (through holes) 110 are formed so as to establish a connection between metal anodes 111 each used for an organic light-emitting device and the source electrodes 17.

An organic layer 112 having a single or multilayer structure and a cathode 113 are stacked, in that order, on the anodes 111, thereby providing the display apparatus 1. To prevent degradation of the organic light-emitting devices, a first protective layer 114 and a second protective layer 115 may be provided. Driving the display apparatus including the organic light-emitting devices according to aspects of the present invention permits a high-quality image to be stably displayed for a long period of time.

The switching elements of the display apparatus are not particularly limited. For example, a single-crystal silicon substrate, a metal-insulator-metal (MIM) element, an amorphous silicon (a-Si) element may be easily used for the display apparatus.

With respect to the direction of light emission from an organic light-emitting device, the organic light-emitting device according to aspects of the present invention may have a bottom-emission structure, in which light emerges from the substrate, or a top-emission structure, in which light emerges from a surface opposite the substrate.

EXAMPLES

While the present invention will be more specifically described below by examples, the present invention is not limited thereto.

Example 1

Synthesis of Compound A6

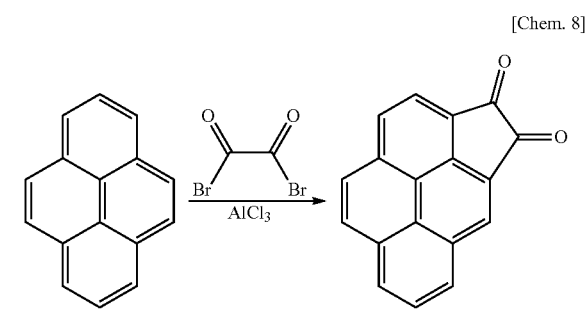

[Chem. 8]

Into a flask filled with nitrogen, 5.01 g (25 mmol) of pyrene and 500 mL of carbon disulfide were charged. After the mixture was stirred at −5° C., 5.4 g (25 mmol) of oxalyl bromide was added thereto.

After 6.6 g (50 mmol) of aluminum chloride was added thereto, the mixture was stirred at −5° C. for 40 minutes. Then the mixture was stirred overnight while warmed to room temperature. The resulting solution was heated to 40° C. to evaporate the solvent. The resulting solid was washed by stirring in 10% aqueous hydrochloric acid. The solid was washed with deionized water and dispersed in an aqueous solution of 4% sodium bisulfite at 80° C. The dispersion was hot-filtered.

Recrystallization from dimethylformamide gave 3.81 g of cyclopenta[cd]pyrene-3,4-dione as needle crystals.

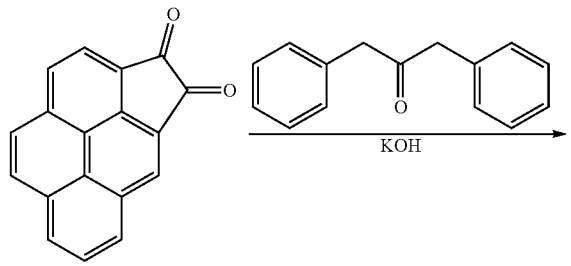

[Chem. 9]

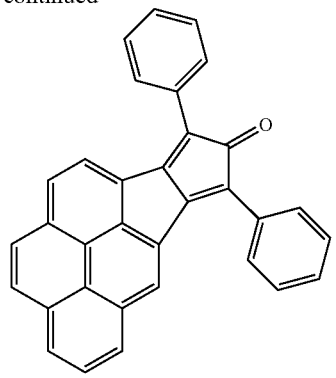

Next, 3 g (11 mmol) of cyclopenta[cd]pyrene-3,4-dione and 2.3 g (11 mmol) of 1,3-diphenylacetone were added to 300 mL of an ethanol/toluene (10/1) solution. Under stirring, 52 mL of 6 N aqueous potassium hydroxide was added dropwise thereto. After the completion of the dropwise addition, the mixture was heated to 50° C., stirred for 1 hour, and cooled. The resulting precipitate was filtered, washed with water, ethanol, and isopropyl alcohol, in that order, and dried by heating under reduced pressure to give 2.85 g of 9,11-diphenyl-10H-pentaleno[1,2,3-cd]pyren-10-one as a black solid.

[Chem. 10]

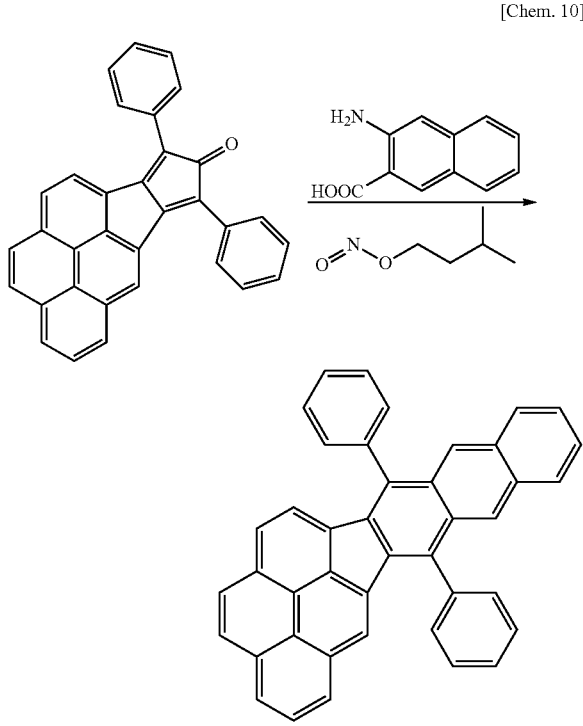

Next, 0.4 g (0.9 mmol) of 9,11-diphenyl-10H-pentaleno[1,2,3-cd]pyren-10-one and 0.2 g (1.1 mmol) of 3-amino-2-naphthoic acid were added to 15 mL of toluene. After the mixture was heated to 80° C., 0.3 mL (2.2 mmol) of isoamyl nitrite was slowly added dropwise thereto. The resulting mixture was heated to 110° C. and stirred for 3 hours.

After cooling, the mixture was washed with two 100-mL portions of water. The resulting solution in the organic phase was washed with saturated brine and dried over magnesium sulfate. The resulting solution was filtered. The filtrate was concentrated to give a dark brown liquid. The liquid was purified by column chromatography (toluene/heptane=4:1) and was then recrystallized to give 0.07 g (yield: 15%) of yellowish green crystals.

The structure of compound A6 was determined by NMR. $^1$H-NMR (CDCl$_3$, 400 MHz), δ (ppm): 8.22 (d, 2H, J=9.16 Hz), 8.13 (d, 1H, J=7.79 Hz), 8.02 (s, 2H), 7.99-7.05 (m, 19H).

The emission spectrum of a 1×10$^{-5}$ mol/L solution of exemplified compound A6 in toluene was obtained by measuring photoluminescence with a spectrofluorometer (Model: F-4500, manufactured by Hitachi Ltd.) at an excitation wavelength of 350 nm. The maximum intensity in the resulting spectrum was observed at 487 nm. The quantum yield was measured using the same solution and found to be 0.85.

Example 2

Synthesis of Compound A7

[Chem. 11]

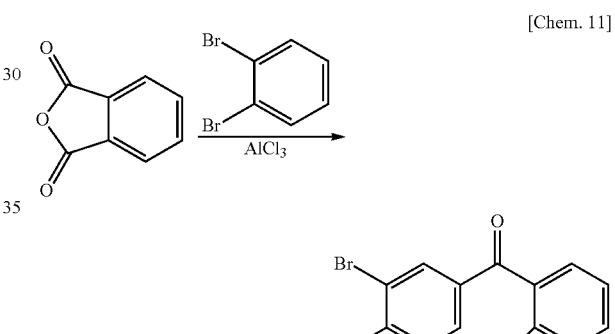

Into a flask filled with nitrogen, 2.96 g (20 mmol) of phthalic anhydride was charged. Then 8 mL of 1,2-dibromobenzene and 5.3 g (40 mmol) of aluminum chloride were added thereto. The mixture was reacted at 150° C. for 1 hour. Next, 2 M aqueous hydrochloric acid and toluene were added to form two phases. To the organic phase, 2 M aqueous sodium hydroxide was added. The separation of two phases was performed.

The aqueous phase was subjected to acidification by the addition of 6 M hydrochloric acid, followed by extraction with ether. The resulting organic phase was washed with water, dried over magnesium sulfate, and concentrated under reduced pressure to give 6.7 g (yield: 87%) of 3',4'-dibromobenzophenonecarboxylic acid.

[Chem. 12]

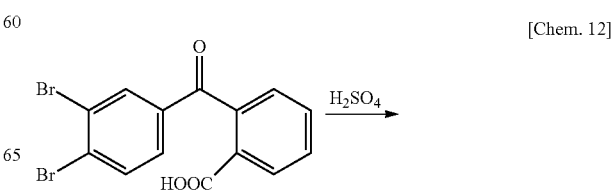

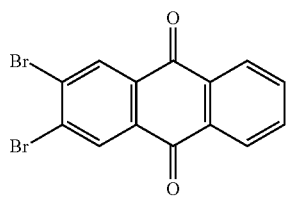

Next, 6.7 g (17.4 mmol) of 3',4'-dibromobenzophenonecarboxylic acid was dissolved in 20 mL of concentrated sulfuric acid. The solution was heated to 125° C. over a period of 1 hour and heated at the same temperature for another 2 hours. The reaction mixture was poured into ice. The resulting precipitate was filtered, washed with water, and dried. The resulting crude product was purified by silica gel column chromatography (methylene chloride/hexane=2/1) to give 1.46 g (yield: 23%) of 2,3-dibromoanthraquinone as a yellow powder.

[Chem. 13]

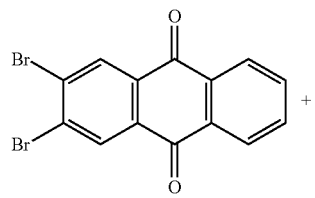

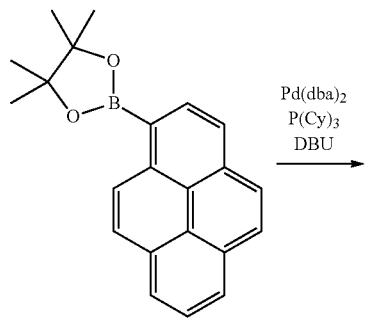

E3

Into a flask, 1.4 g (3.8 mmol) of 2,3-dibromoanthraquinone, 1.5 g (4.6 mmol) of 4,4,5,5-tetramethyl-2-(pyren-1-yl)-1,3,2-dioxaborolane, 0.22 g (0.38 mmol) of bis(dibenzylideneacetone)palladium (Pd(dba)$_2$), 0.27 g (0.95 mmol) of tricyclohexylphosphine (P(Cy)$_3$), and 50 mL of dimethylformamide were charged.

After air in a flask was replaced with nitrogen gas, 1.2 mL (7.6 mmol) of diazabicycloundecene (DBU) was added thereto. The mixture was reacted at 155° C. for 6 hours. After cooling to room temperature, chloroform was added thereto.

The mixture was washed with a saturated aqueous sodium chloride solution. The organic phase was dried over sodium sulfate. The organic phase was concentrated under reduced pressure and purified by silica gel column chromatography (toluene/heptane=7/3) to give 0.85 g (yield: 55%) of compound E3 described above.

[Chem. 14]

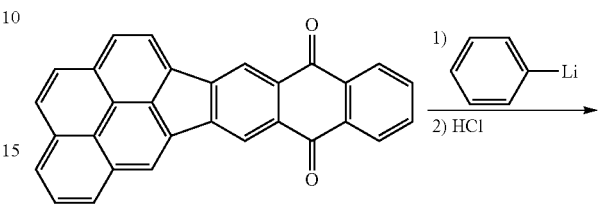

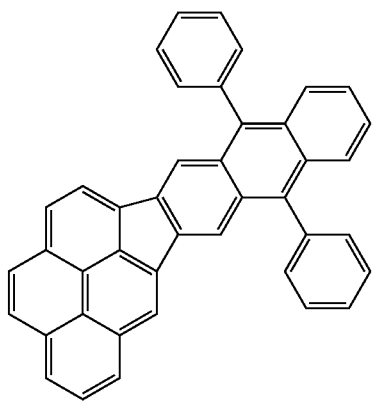

Into a flask filled with nitrogen, 0.85 g (2.1 mmol) of compound E3 and 20 mL of dry tetrahydrofuran were charged. The mixture was cooled to −50° C. Then 0.3 mL (2.7 mmol) of n-butyllithium was added dropwise from a syringe. After the completion of the dropwise addition, the mixture was stirred for 1 hour, returned to room temperature, and stirred for another 3 hours. Then 10 mL of 33% hydrochloric acid was added thereto. The mixture was refluxed for 2 hours. The resulting precipitate was filtered, washed with water and then methanol, and dissolved in toluene. The solution was dried over magnesium sulfate, concentrated, and purified by silica gel column chromatography (toluene/heptane=7/3) to give 0.69 g (yield: 62%) of exemplified compound A7.

The emission spectrum of a $1 \times 10^{-5}$ mol/L solution of exemplified compound A7 in toluene was obtained by measuring photoluminescence with a spectrofluorometer (Model: F-4500, manufactured by Hitachi Ltd.) at an excitation wavelength of 350 nm. The maximum intensity in the resulting spectrum was observed at 492 nm.

The quantum yield was measured using the same solution and found to be 0.84.

Example 3

Synthesis of Compound A19

The same reaction and purification as those in Example 2 were performed, except that 2-(7-(3,5-di-tert-butylphenyl)pyren-1-yl)-4,4,5,5-tetramethyl-1,3,2-dioxaborolane was used instead of 4,4,5,5-tetramethyl-2-(pyren-1-yl)-1,3,2-dioxaborolane.

The emission spectrum of a $1 \times 10^{-5}$ mol/L solution of exemplified compound A19 in toluene was obtained by measuring photoluminescence with a spectrofluorometer (Model: F-4500, manufactured by Hitachi Ltd.) at an excitation wavelength of 350 nm. The maximum intensity in the resulting spectrum was observed at 489 nm.

The quantum yield was measured using the same solution and found to be 0.82.

Example 4

Synthesis of Compound A45

The same reaction and purification as those in Example 1 were performed, except that 3-tert-butylpyrene was used instead of pyrene.

The emission spectrum of a $1 \times 10^{-5}$ mol/L solution of exemplified compound A45 in toluene was obtained by measuring photoluminescence with a spectrofluorometer (Model: F-4500, manufactured by Hitachi Ltd.) at an excitation wavelength of 350 nm. The maximum intensity in the resulting spectrum was observed at 487 nm.

The quantum yield was measured using the same solution and found to be 0.84.

Example 5

Synthesis of Compound A46

The same reaction and purification as those in Example 2 were performed, except that 2-(7-tert-butylpyren-1-yl)-4,4,5,5-tetramethyl-2-(pyren-1-yl)-1,3,2-dioxaborolane was used instead of 4,4,5,5-tetramethyl-2-(pyren-1-yl)-1,3,2-dioxaborolane.

The emission spectrum of a $1 \times 10^{-5}$ mol/L solution of exemplified compound A46 in toluene was obtained by measuring photoluminescence with a spectrofluorometer (Model: F-4500, manufactured by Hitachi Ltd.) at an excitation wavelength of 350 nm. The maximum intensity in the resulting spectrum was observed at 487 nm.

The quantum yield was measured using the same solution and found to be 0.82.

Examples 6 to 14

In each of Examples 6 to 14, the multilayer organic light-emitting device (anode/hole injection layer/hole transport layer/light-emitting layer/hole-exciton-blocking layer/electron transport layer/cathode) of the fifth example was used. An ITO film having a thickness of 100 nm was formed by patterning on a glass substrate. Organic layers and electrode layers described below were formed on the ITO film by vacuum evaporation using resistance heating in a vacuum chamber at $10^{-5}$ Pa. Continuous film formation was performed in such a manner that the area of the facing electrodes was 3 mm².
Hole transport layer (30 nm): compound G-1 described below
Light-emitting layer (30 nm):
   host compound: compound described in Table 4,
   dopant: exemplified compound described in Table 4 (dopant content of light-emitting layer: 5% by weight)
   hole-exciton-blocking layer (10 nm): compound G-3 described below
Electron transport layer (30 nm): compound G-4 described below
Metal electrode layer 1 (1 nm): LiF
Metal electrode layer 2 (100 nm): Al

[Chem. 15]

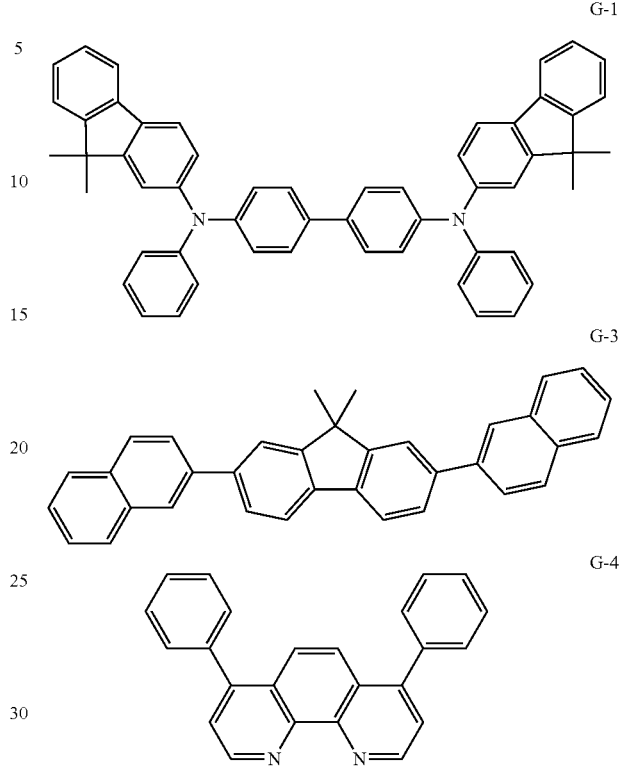

With respect to the properties of each organic light-emitting device, the current-voltage characteristics were measured with a micro-current meter (Model: 4140B, manufactured by Hewlett-Packard Corp). The luminance was measured with a luminance meter (Model: BM7, manufactured by Topcon Corp).

Table 4 shows the luminous efficiency and the voltage when each of the devices of Examples 6 to 14 was driven so as to emit light with a luminance of 1000 cd/m². Host materials described in Table 4 are compounds described in Table 3.

TABLE 4

| | Dopant | Host compound | Luminous efficiency (cd/A) | Voltage (V) |
|---|---|---|---|---|
| Example 6 | A6 | H24 | 9.4 | 7.2 |
| Example 7 | A7 | H8 | 9.5 | 7.2 |
| Example 8 | A10 | H10 | 9.1 | 7.5 |
| Example 9 | A17 | H27 | 9.1 | 7.7 |
| Example 10 | A19 | H9 | 9.0 | 7.6 |
| Example 11 | A35 | H19 | 8.3 | 8.5 |
| Example 12 | A45 | H21 | 9.6 | 7.1 |
| Example 13 | A46 | H21 | 8.9 | 8.1 |
| Example 14 | B3 | H23 | 8.6 | 8.3 |

Examples 15 to 20

In each of Examples 15 to 20, an image display apparatus including the multilayer organic light-emitting device (anode/hole injection layer/hole transport layer/light-emitting layer/hole-exciton-blocking layer/electron transport layer/cathode) of the fifth example was used.

TFTs were formed on a glass substrate. A thin film composed of silicon nitride was formed thereon by CVD to protect the TFTs. An acrylic negative resist was applied onto the substrate, prebaked, and exposed through a photomask so as to form through-holes configured to drive all pixels to emit light. Development was performed by immersion in an etching solution, followed by post-baking to form a planarization film on the TFTs.

A 200-nm-thick aluminum film was formed by sputtering with a metal mask so as to form pixels at regular intervals. A 100-nm-thick ITO film was formed by sputtering so as to cover the aluminum film, thereby resulting in a first electrode. The substrate was heated at 130° C. for 4 hours under a vacuum of $1\times10^{-5}$ Pa for dehydration. After the completion of the dehydration, silicon nitride was stacked by CVD with a metal mask so as to form an insulating film in a region other than the pixels and extraction electrode, resulting in a pixel separation film. Thereby, a TFT substrate before stacking organic light-emitting devices was produced.

Organic layers described below were continuously formed by vacuum evaporation using resistance heating in a vacuum chamber with a vacuum of $10^{-5}$ Pa. Then IZO was deposited by sputtering to form a 30-nm-thick transparent electrode as a cathode.

Hole injection layer (95 nm): compound G-11 described below

Hole transport layer (10 nm): compound G-12 described below

Light-emitting layer (35 nm):
   host compound: compound described in Table 5
   dopant: exemplified compound described in Table 5 (dopant content with respect to host compound: 2% by weight)

Electron transport layer (10 nm): compound G-14 described below

Electron injection layer (70 nm):
   compound G-15 described below (80% by weight)
   Li: (20% by weight)

A UV-curable sealing agent was applied to the periphery in a nitrogen atmosphere. A drying agent to absorb water was applied to a cover glass so as to be located at the inner circumference of the sealing agent. The cover glass was bonded to the TFT substrate. The sealing agent was cured by irradiation with ultraviolet rays for 6 minutes, thereby providing an image display apparatus.

[Chem. 16]

G-11

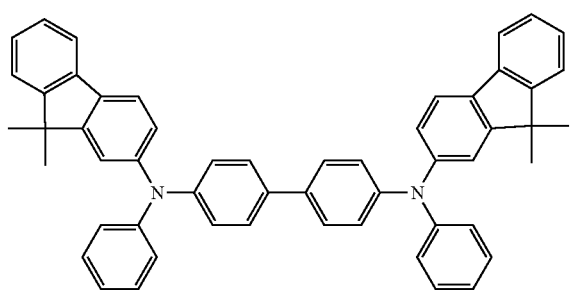

G-12

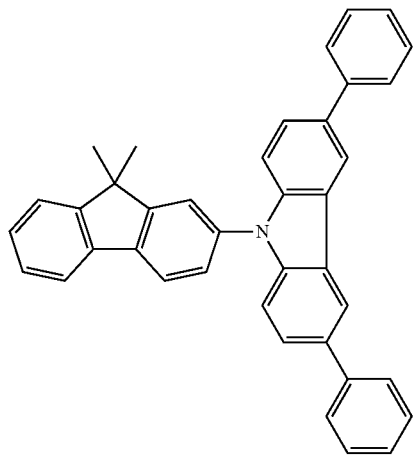

G-14

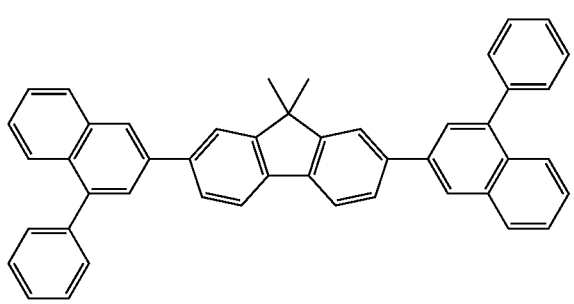

G-15

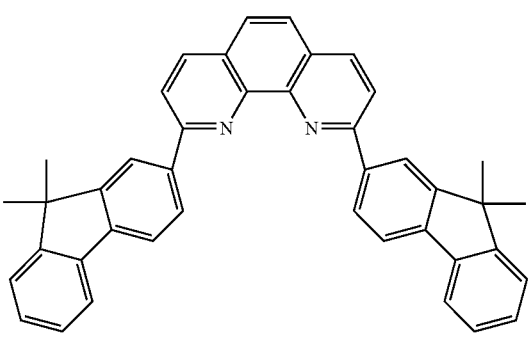

With respect to the properties of each organic light-emitting device, the current-voltage characteristics were measured with a micro-current meter (Model: 4140B, manufactured by Hewlett-Packard Corp). The luminance was measured with a luminance meter (Model: BM7, manufactured by Topcon Corp).

Table 5 shows the luminous efficiency and the voltage when the each of the image display apparatuses of Examples 15 to 20 was driven so as to emit light with a luminance of 1000 cd/m².

TABLE 5

| | Dopant | Host compound | Luminous efficiency (cd/A) | Voltage (V) |
|---|---|---|---|---|
| Example 15 | A5 | H27 | 8.9 | 9.5 |
| Example 16 | A6 | H9 | 9.0 | 9.3 |
| Example 17 | A18 | H10 | 8.9 | 9.5 |
| Example 18 | A20 | H8 | 9.0 | 9.4 |
| Example 19 | A45 | H28 | 9.1 | 9.2 |
| Example 20 | A46 | H21 | 9.2 | 9.1 |

RESULTS AND DISCUSSION

The organic compound according to aspects of the present invention has a high quantum yield and emits light suitable for green. The use of the organic compound as a dopant results in an organic light-emitting device and an image display apparatus having satisfactory light-emitting properties.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-174838, filed Aug. 3, 2010, which is hereby incorporated by reference herein in its entirety.

The invention claimed is:

1. A naphtho[2',3':5,6]indeno[1,2,3-cd]pyrene derivative represented by general formula (1):

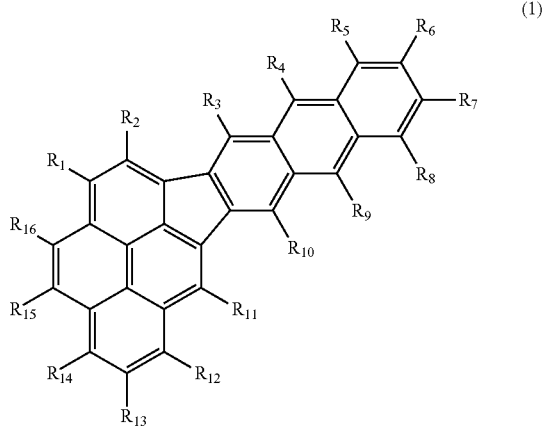

wherein in general formula (1), $R_1$ to $R_{16}$ are each independently selected from a hydrogen atom, a halogen atom, substituted or unsubstituted alkyl groups, substituted or unsubstituted alkoxy groups, substituted or unsubstituted amino groups, substituted or unsubstituted aryl groups, and substituted or unsubstituted heterocyclic groups, and at least one of $R_3$, $R_4$, $R_9$, and $R_{10}$ is selected from substituted or unsubstituted aryl groups and substituted or unsubstituted heterocyclic groups.

2. The derivative according to claim 1,
wherein one of $R_3$ and $R_4$ is selected from substituted or unsubstituted aryl groups, and the other is selected from a hydrogen atom and a halogen atom, and
wherein one of $R_9$ and $R_{10}$ is selected from substituted or unsubstituted aryl groups, and the other is selected from a hydrogen atom and a halogen atom.

3. An organic light-emitting device comprising:
a pair of electrodes;
an organic compound layer disposed between the pair of electrodes comprising the naphtho[2',3':5,6]indeno[1,2,3-cd]pyrene derivative according to claim 1.

4. An image display apparatus comprising:
the organic light-emitting device according to claim 3; and
a thin-film transistor configured to feed an electric signal to the organic light-emitting device.

5. An illuminating apparatus comprising a substrate and the organic light-emitting device according to claim 3.

6. The organic light-emitting device according to claim 3,
wherein the organic compound layer is a light-emitting layer comprising a host and a guest, and
wherein the guest is the naphtho[2',3':5,6]indeno[1,2,3-cd]pyrene derivative.

7. An apparatus comprising a substrate and the organic light-emitting device according to claim 3.

8. The apparatus according to claim 7,
further comprising a color filter.

9. An electrophotographic image forming apparatus comprising an exposure light source;
the exposure light source comprising a plurality of the organic light-emitting devices according to claim 3, and
the plurality of the organic light-emitting devices being arranged in a line.

10. A light source configured to expose a latent image on a photosensitive member of an electrophotographic image-forming apparatus comprising the organic light-emitting device according to claim 3.

* * * * *